US008855750B2

(12) United States Patent
Teramura

(10) Patent No.: US 8,855,750 B2
(45) Date of Patent: Oct. 7, 2014

(54) OPTICAL THREE-DIMENSIONAL STRUCTURE MEASURING DEVICE AND STRUCTURE INFORMATION PROCESSING METHOD THEREFOR

(75) Inventor: Yuichi Teramura, Kanagawa (JP)

(73) Assignee: Topcon Corporation, Tokyo (JP)

( * ) Notice: Subject to any disclaimer, the term of this patent is extended or adjusted under 35 U.S.C. 154(b) by 139 days.

(21) Appl. No.: 13/257,573

(22) PCT Filed: Mar. 3, 2010

(86) PCT No.: PCT/JP2010/053398
§ 371 (c)(1),
(2), (4) Date: Sep. 19, 2011

(87) PCT Pub. No.: WO2010/106913
PCT Pub. Date: Sep. 23, 2010

(65) Prior Publication Data
US 2012/0010494 A1    Jan. 12, 2012

(30) Foreign Application Priority Data
Mar. 19, 2009   (JP) ................. 2009-068557

(51) Int. Cl.
*A61B 5/00*   (2006.01)
*G01B 9/02*   (2006.01)
*A61B 3/00*   (2006.01)
*A61B 3/10*   (2006.01)
*G01N 21/47*   (2006.01)

(52) U.S. Cl.
CPC .......... *G01B 9/02069* (2013.01); *A61B 5/0084* (2013.01); *G01B 9/02004* (2013.01); *A61B 3/00* (2013.01); *A61B 5/7264* (2013.01); *A61B 3/1005* (2013.01); *A61B 3/102* (2013.01); *A61B 5/0066* (2013.01); *G01B 9/02091* (2013.01); *G01N 21/4795* (2013.01); *G01B 9/02088* (2013.01); *A61B 5/0059* (2013.01); *G01B 9/02085* (2013.01); *A61B 5/7203* (2013.01); *G01B 2290/65* (2013.01)
USPC ........................................... 600/476; 356/450

(58) Field of Classification Search
USPC .................................. 600/473, 476; 356/450
See application file for complete search history.

(56) References Cited

U.S. PATENT DOCUMENTS

2007/0216909 A1   9/2007   Everett et al.
2007/0285619 A1   12/2007   Aoki et al.
2008/0117427 A1   5/2008   Teramura et al.

FOREIGN PATENT DOCUMENTS

| JP | 5-176925 A | 7/1993 |
| JP | 2005-218676 A | 8/2005 |
| JP | 2007-325831 A | 12/2007 |
| JP | 2008-73099 A | 4/2008 |
| JP | 2008-128708 A | 6/2008 |
| JP | 2008-194106 A | 8/2008 |

OTHER PUBLICATIONS

Ishikawa et al. "Macular Segmentation with Optical Coherence Tomography". Investigative Ophthalmology & Visual Science, Jun. 2005, vol. 46, No. 6 pp. 2012-2017.*
Hsiung et al. "Ultrahigh-resolution and 3-dimensional optical coherence tomography ex vivo imaging of the large and small intestines". vol. 62, No. 4 : 2005 Gastrointestinal Endoscopy pp. 561-574.*
Testoni et al. "Optical Coherence Tomography for Investigation of the Pancreatico-Biliary System: Still Experimental?". JOP. Journal of the Pancreas—http://www.joplink.net—vol. 8, No. 2—Mar. 2007 pp. 156-165.*
European Search Report dated Aug. 2, 2012.
Florian Bazant-Hegemark, et al.: "Towards Automated Classification of Clinical Optical Coherence Tomography Data of Dense Tissues", Lasers in Medical Science, Springer-Verlag, Lo, vol. 24, No. 4, Oct. 21, 2008, pp. 627-638, XP019663598, ISSN:1435-604X.
Delia Cabrera Fernandez, et al.: "Automated Detection of Retinal Layers Structures on Optical Coherence Tomography Images", Optics Express, vol. 13, No. 25, Jan. 1, 2005, pp. 10200-10216, XP55033807, ISSN: 1094-4087, DOI: 10.1364/OPEX.13.010200.
Zara Jason M., et al.: "Endoscopic OCT Approaches Toward Cancer Diagnosis", IEEE Journal of Selected Topics in Quantum Electronics, IEEE Service Center, Piscataway, NJ, US, vol. 14, No. 1, Jan. 1, 2008, pp. 70-81, XP011204194, ISSN: 1077-260X.
Chinese Office Action dated Apr. 18, 2013 with an English translation.
Hiroshi Ishikawa et al, "Macular Segmentation with Optical Coherence Tomography", Investigative Ophthalmology & Visual Science, Jun. 2005, vol. 46, No. 6, pp. 2012-2017.
Pier Alberto Testoni et al, "Optical Coherence Tomography for Investigation of the Pancreatico-Biliary System: Still Experimental?" JOP. Journal of the Pancreas, Mar. 2007, vol. 8, No. 2 pp. 156-165.
PCT/ISA/237 (written opinion of the international searching authority with English translation, dated Apr. 6, 2010).
PCT/IB/326, Apr. 6, 2010.
PCT/IB/338, Apr. 6, 2010.
PCT/IB/373, Apr. 6, 2010.

* cited by examiner

*Primary Examiner* — Unsu Jung
*Assistant Examiner* — Phong K Huynh
(74) *Attorney, Agent, or Firm* — McGinn IP Law Group, PLLC

(57) ABSTRACT

An optical three-dimensional structure measuring device including: optical three-dimensional structure information storing device (91) for storing optical three-dimensional structure information; specific layer extracting device (121) for comparing information values of the optical three-dimensional structure information stored in the optical three-dimensional structure information storing device with a predetermined threshold and extracting, as a specific layer area of the measurement target, an area equal to or greater than a predetermined range where the information values of the optical three-dimensional structure information equal to or greater than the predetermined threshold continue; missing area extracting device (122) for extracting, as missing areas, areas where the information values of the optical three-dimensional structure information are smaller than the predetermined threshold in the specific layer area; missing area range calculating device (123) for calculating sizes of ranges of the missing areas; and region-of-interest classifying device (124) for comparing the sizes of the ranges of the missing areas with a plurality of predetermined range determination reference values and classifying the missing areas into a plurality of types of regions of interest.

20 Claims, 14 Drawing Sheets

OPTICAL THREE-DIMENSIONAL STRUCTURE MEASURING DEVICE AND STRUCTURE INFORMATION PROCESSING METHOD THEREFOR

This Application claims priority based under the Patent Cooperation Treaty from International Patent Application No. PCT/JP2010/053398 filed on Mar. 3, 2010 and under the International (Paris) Convention from Japanese Patent Application No. 2009-068557 filed on Mar. 19, 2009.

TECHNICAL FIELD

The present invention relates to an optical three-dimensional structure measuring device and a structure information processing method therefor, and particularly, to an optical three-dimensional structure measuring device and a structure information processing method therefor characterized by a processing part of structure information of a measurement target.

BACKGROUND ART

Conventionally, an optical tomographic image acquiring device using OCT (Optical Coherence Tomography) measurement is used in some cases to acquire an optical tomographic image of living tissues. The optical tomographic image acquiring device divides low-coherence light emitted from a light source into measurement light and reference light and then multiplexes reflected light, which is from a measurement target when the measurement light is directed to the measurement target, or backscattered light and the reference light to acquire an optical tomographic image based on the intensity of interference light of the reflected light and the reference light (Patent Literature 1). Hereinafter, the reflected light from the measurement target and the backscattered light will be collectively described as reflected light.

There are roughly two types of OCT measurement, TD-OCT (Time domain OCT) measurement and FD-OCT (Fourier Domain OCT) measurement. The TD-OCT measurement is a method of measuring the interference light intensity while changing the optical path length of the reference light to acquire a reflected light intensity distribution corresponding to the position in a depth direction (hereinafter, called "depth position") of the measurement target.

Meanwhile, the FD-OCT measurement is a method of measuring the interference light intensity of each spectral component of light without changing the optical path length of the reference light and the signal light, and a computer applies a frequency analysis represented by a Fourier transform to a spectral interference intensity signal obtained here to acquire the reflected light intensity distribution corresponding to the depth position. The PD-OCT measurement is recently drawing attention as a method that allows high-speed measurement, because mechanical scanning that exists in the TD-OCT is not necessary.

Typical examples of device configurations for performing the FD-OCT measurement include two types, an SD-OCT (Spectral Domain OCT) device and an SS-OCT (Swept Source OCT). The SD-OCT device uses wideband low-coherence light, such as an SLD (Super Luminescence Diode), an ASE (Amplified Spontaneous Emission) light source, and white light, as a light source, uses a Michelson interferometer or the like to divide the wideband low-coherence light into measurement light and reference light, directs the measurement light to a measurement target, interferes reflected light returned at that time and the reference light, uses a spectrometer to dissolve the interference light into frequency components, uses a detector array including elements such as photodiodes arranged in an array to measure the interference light intensity of each frequency component, and applies a Fourier transform to an obtained spectral interference intensity signal by a computer to thereby form an optical tomographic image.

Meanwhile, the SS-OCT device uses a laser that temporally sweeps the optical frequency as a light source, interferes reflected light and reference light at each wavelength, measures the time waveform of a signal corresponding to the time change of the optical frequency, and applies a Fourier transform to an obtained spectral interference intensity signal by a computer to thereby form an optical tomographic image.

Although the OCT measurement is a method for acquiring an optical tomographic image of a specific area as described above, an endoscope can determine the extent of the invasion of a cancer lesion by, for example, detecting the cancer lesion through observation by a normal illumination light endoscope or a special light endoscope and applying an OCT measurement to the area. The optical axis of the measurement light can be two-dimensionally scanned to acquire three-dimensional information along with depth information based on the OCT measurement.

Integration of the OCT measurement and a three-dimensional computer graphic technique allows displaying a three-dimensional structure model with micrometer-order resolving power. Therefore, the three-dimensional structure model based on the OCT measurement will be called an optical three-dimensional structure image.

For example, the cancer invasion depth of esophagus is observed by the OCT. An OCT image of esophagus depicts, from the near side, a thin epithelial layer and a strongly scattered basement membrane, relatively strongly scattered lamina propria mucosae below the epithelial layer and the basement membrane, and relatively weakly scattered muscularis mucosae, a strongly scattered submucosal layer, as well as a weakly scattered muscular layer below the lamina propria mucosae.

An example of a tissue structure change caused by the development of cancer will be described. Epithelium hypertrophy is developed when the cancer develops and grows on the epithelial layer. It is known that at this period, new blood vessels extend from blood vessels in a submucosal layer to the mucosal layer, toward the cancer, and the new blood vessels are formed around the cancer cells beyond the basement membrane. When the cancer progresses, the cancer breaks the basement membrane to invade the lamina propria, and if the cancer further progresses, the invasion depth increases toward the muscularis mucosae, the submucosal layer, and the muscular layer.

The cancer that has not invaded the basement membrane is called an "intraepithelial neoplasm", which serves as an indication that the cancer will be cured if removed. It is important to determine whether the cancer has invaded below the basement membrane to detect an early-stage cancer earlier for a minimally invasive treatment of the cancer before there is a risk of spreading. If the cancer has invaded beyond the basement membrane, whether the cancer has invaded beyond the muscularis mucosae is important as the next indication. The possibility of metastasis is low if the cancer is not beyond the muscularis mucosae, and an endoscopic ablative therapy is selected. On the other hand, the possibility of metastasis is high if the cancer is beyond the muscularis mucosae, and an open-chest surgery or a radiation therapy is selected. It is important to determine whether the cancer has invaded below the muscularis mucosae for a minimally invasive treatment of an early-stage cancer. Therefore, it is expected to extract and image only a specific membrane or layer, such as a basement membrane or muscularis mucosae. However, there is no method of directly observing the state of the basement membrane.

A method of extracting a specific scattering intensity of, for example, ocular fundus by the OCT to extract a layer structure is disclosed (Patent Literature 2). To extract the layer structure, a one-dimensional differential filter or the like in a depth direction is specifically used to extract the layer structure or the boundary of the layer. The layer structure of the ocular fundus is clear, and there is a little change in the structure. Therefore, there is not much error in the extraction based on the method. However, there is no example of the implementation of the method in digestive tracts, such as esophagus.

It is known that if cancer develops on the epithelial layer, new blood vessels are formed on the mucosal layer toward the cancer. In the case of early-stage cancer of esophagus, the new blood vessels pass through the submucosal layer and the basement membrane to extend to the mucosal epithelial layer to form an IPCL (intra-epithelial papillary capillary loop). If the cancer progresses, the cancer breaks the basement membrane and enters the submucosal layer. The new blood vessels are formed in random directions toward the cancer. In normal endoscopy, a method of determining the grade of cancer from the density distribution and the shapes of new blood vessels that can be seen through from the surface is implemented.

CITATION LIST

Patent Literature

{PTL 1} Japanese Patent Application Laid-Open No. 2008-128708
{PTL 2} Japanese Patent Application Laid-Open No. 2008-73099

SUMMARY OF INVENTION

Technical Problem

A signal indicating the basement membrane is observed in the tomographic image of OCT. However, the extraction may be difficult in the case of the esophageal mucosa due to a false recognition caused by structures in mucosa, such as new blood vessels, that indicate strong scatter as in the basement membrane or due to attenuation of the light intensity at a deeper location caused by extreme thickening after progression to cancer or caused by structures of a relatively shallow layer such as blood vessels. There is a case in which the basement membrane is lost due to the invasion of cancer, and there is a disadvantage that it is difficult to recognize whether a layer other than the basement membrane or another layer emerged from a structure is continuous or discontinuous with the basement membrane.

The distribution of new blood vessels is a useful indication in recognizing the spread of cancer. However, the conventional OCT measurement methods only observe whether the density of new blood vessels approaching the mucosal surface stands out compared to surrounding normal sections. Meanwhile, the conventional endoscopic observation methods only observe new blood vessels approaching the mucosal surface.

Therefore, the conventional methods have disadvantages that the distinction from the new blood vessels is difficult when, for example, there is a congestion caused by inflammation and that the visibility is poor when noncancerous mucosa covers the mucosa. For example, it is expected to be able to accurately determine the distribution of the new blood vessels inside the living body if holes created when the new blood vessels exceed the basement membrane can be directly observed. However, there has not been such a method.

The present invention has been made in view of the forgoing circumstances, and an object of the present invention is to provide an optical three-dimensional structure measuring device and a structure information processing method therefor that can easily identify the continuity of layer areas based on structure information of a measurement target with a layer structure and that can surely extract structure information of an unclear layer area at a deep section caused by a structure of a shallow layer area.

Solution to Problem

To attain the object, a first aspect provides an optical three-dimensional structure measuring device that directs measurement light in a depth direction of a lamination of a measurement target with a layer structure and that two-dimensionally scans an optical axis of the measurement light to acquire optical three-dimensional structure information of the measurement target, the optical three-dimensional structure measuring device including: optical three-dimensional structure information storing device for storing the optical three-dimensional structure information; specific layer extracting device for comparing information values of the optical three-dimensional structure information stored in the optical three-dimensional structure information storing device with a predetermined threshold and extracting, as a specific layer area of the measurement target, an area equal to or greater than a predetermined range where the information values of the optical three-dimensional structure information equal to or greater than the predetermined threshold continue; missing area extracting device for extracting, as missing areas, areas where the information values of the optical three-dimensional structure information are smaller than the predetermined threshold in the specific layer area; missing area range calculating device for calculating sizes of ranges of the missing areas; and region-of-interest classifying device for comparing the sizes of the ranges of the missing areas with a plurality of predetermined range determination reference values and classifying the missing areas into a plurality of types of regions of interest.

In the optical three-dimensional structure measuring device of the first aspect, the specific layer extracting device compares information values of the optical three-dimensional structure information stored in the optical three-dimensional structure information storing device with a predetermined threshold and extracts, as a specific layer area of the measurement target, an area equal to or greater than a predetermined range where the information values of the optical three-dimensional structure information equal to or greater than the predetermined threshold continue. The missing area extracting device extracts, as missing areas, areas where the information values of the optical three-dimensional structure information are smaller than the predetermined threshold in the specific layer area. The missing area range calculating device calculates sizes of ranges of the missing areas. The region-of-interest classifying device compares the sizes of the ranges of the missing areas with a plurality of predetermined range determination reference values and classifies the missing areas into a plurality of types of regions of interest. As a result, there are advantageous effects that the continuity of layer areas can be easily identified from structure information of a measurement target with a layer structure and that structure information of an unclear layer area at a deep section caused by a structure in a shallow layer area can be surely extracted.

Preferably, a second aspect provides the optical three-dimensional structure measuring device according to the first aspect, wherein the specific layer extracting device comprises noise area deleting device for determining an area as a noise area to delete the area from the optical three-dimensional structure information if the area where the information values of the optical three-dimensional structure information equal to or greater than the predetermined threshold continue is smaller than the predetermined range.

Preferably, a third aspect provides the optical three-dimensional structure measuring device according to the first or second aspect, further including computer graphic image building device for applying a rendering process to the optical three-dimensional structure information to build a computer graphic image.

Preferably, a fourth aspect provides the optical three-dimensional structure measuring device according to the third aspect, including attribute adding device for adding attributes that can identify the specific layer area and the regions of interest to the specific layer area and the regions of interest, wherein the computer graphic image building device applies a rendering process to the optical three-dimensional structure information to build the computer graphic image including the specific layer area and the regions of interest at least provided with the attributes.

Preferably, a fifth aspect provides the optical three-dimensional structure measuring device according to the fourth aspect, wherein the computer graphic image building device builds, as the computer graphic image, a projection image projecting the specific layer area in the depth direction of the lamination of the measurement target.

Preferably, a sixth aspect provides the optical three-dimensional structure measuring device according to the fourth or fifth aspect, wherein the computer graphic image building device applies a rendering process to the optical three-dimensional structure information to build an optical three-dimensional structure image as the computer graphic image.

Preferably, a seventh aspect provides the optical three-dimensional structure measuring device according to any of the fourth to sixth aspects, wherein the attribute adding device includes attribute controlling device for setting, as the attribute of the specific layer area, an attribute of the regions of interest smaller than a minimum range determination reference value at least among the predetermined range determination reference values.

Preferably, an eighth aspect provides the optical three-dimensional structure measuring device according to the seventh aspect, wherein the attribute controlling device adds different attributes to each of the regions of interest classified by the region-of-interest classifying device based on a plurality of range determination reference values with values greater than the minimum range determination reference value among the predetermined range determination reference values.

Preferably, a ninth aspect provides the optical three-dimensional structure measuring device according to any of the first to eighth aspects, wherein the measurement target is living mucosal tissues, and the region-of-interest classifying device classifies the region of interest that is equal to or greater than a first range determination reference value and that is smaller than a second range determination reference value, which is greater than the first range determination reference value, among the predetermined range determination reference values into a new blood vessel area.

Preferably, a tenth aspect provides the optical three-dimensional structure measuring device according to the ninth aspect, wherein the region-of-interest classifying device classifies the region of interest that is equal to or greater than the second range determination reference value among the predetermined range determination reference values into a cancer invasion area.

Preferably, an eleventh aspect provides the optical three-dimensional structure measuring device according to the ninth or tenth aspect, further including new blood vessel distribution image generating device for generating a distribution of the new blood vessel area determined by the region-of-interest classifying device as a new blood vessel distribution image in the specific layer area.

Preferably, a twelfth aspect provides the optical three-dimensional structure measuring device according to any of the ninth to eleventh aspects, wherein the specific layer area includes at least one of a basement membrane area and a muscularis mucosae area of the living mucosal tissues.

A thirteenth aspect provides a structure information processing method of an optical three-dimensional structure measuring device that directs measurement light in a depth direction of a lamination of a measurement target with a layer structure and that two-dimensionally scans an optical axis of the measurement light to acquire optical three-dimensional structure information of the measurement target, the structure information processing method including: optical three-dimensional structure information storing step of storing the optical three-dimensional structure information; specific layer extracting step of comparing information values of the optical three-dimensional structure information stored in the optical three-dimensional structure information storing step with a predetermined threshold and extracting, as a specific layer area of the measurement target, an area equal to or greater than a predetermined range where the information values of the optical three-dimensional structure information equal to or greater than the predetermined threshold continue; missing area extracting step of extracting, as missing areas, areas where the information values of the optical three-dimensional structure information are smaller than the predetermined threshold in the specific layer area; missing area range calculating step of calculating sizes of ranges of the missing areas; and region-of-interest classifying step of comparing the sizes of the ranges of the missing areas with a plurality of predetermined range determination reference values and classifying the missing areas into a plurality of types of regions of interest.

In the structure information processing method of the optical three-dimensional structure measuring device of the thirteenth aspect, the specific layer extracting step compares information values of the optical three-dimensional structure information stored in the optical three-dimensional structure information storing step with a predetermined threshold and extracts, as a specific layer area of the measurement target, an area equal to or greater than a predetermined range where the information values of the optical three-dimensional structure information equal to or greater than the predetermined threshold continue. The missing area extracting step extracts, as missing areas, areas where the information values of the optical three-dimensional structure information are smaller than the predetermined threshold in the specific layer area. The missing area range calculating step calculates sizes of ranges of the missing areas. The region-of-interest classifying step compares the sizes of the ranges of the missing areas with a plurality of predetermined range determination reference values and classifies the missing areas into a plurality of types of regions of interest. As a result, there are advantageous effects that the continuity of layer areas can be easily identified from structure information of a measurement target with a layer structure and that structure information of an unclear layer area at a deep section caused by a structure in a shallow layer area can be surely extracted.

Advantageous Effects of Invention

As described, the present invention have advantageous effects that the continuity of layer areas can be easily identified based on structure information of a measurement target with a layer structure and that structure information of an unclear layer area at a deep section caused by a structure of a shallow layer area can be surely extracted.

DESCRIPTION OF EMBODIMENTS

Hereinafter, an embodiment of an optical three-dimensional structure imaging device as an optical three-dimensional structure measuring device according to the present invention will be described in detail with reference to the attached drawings.

Figure 1:
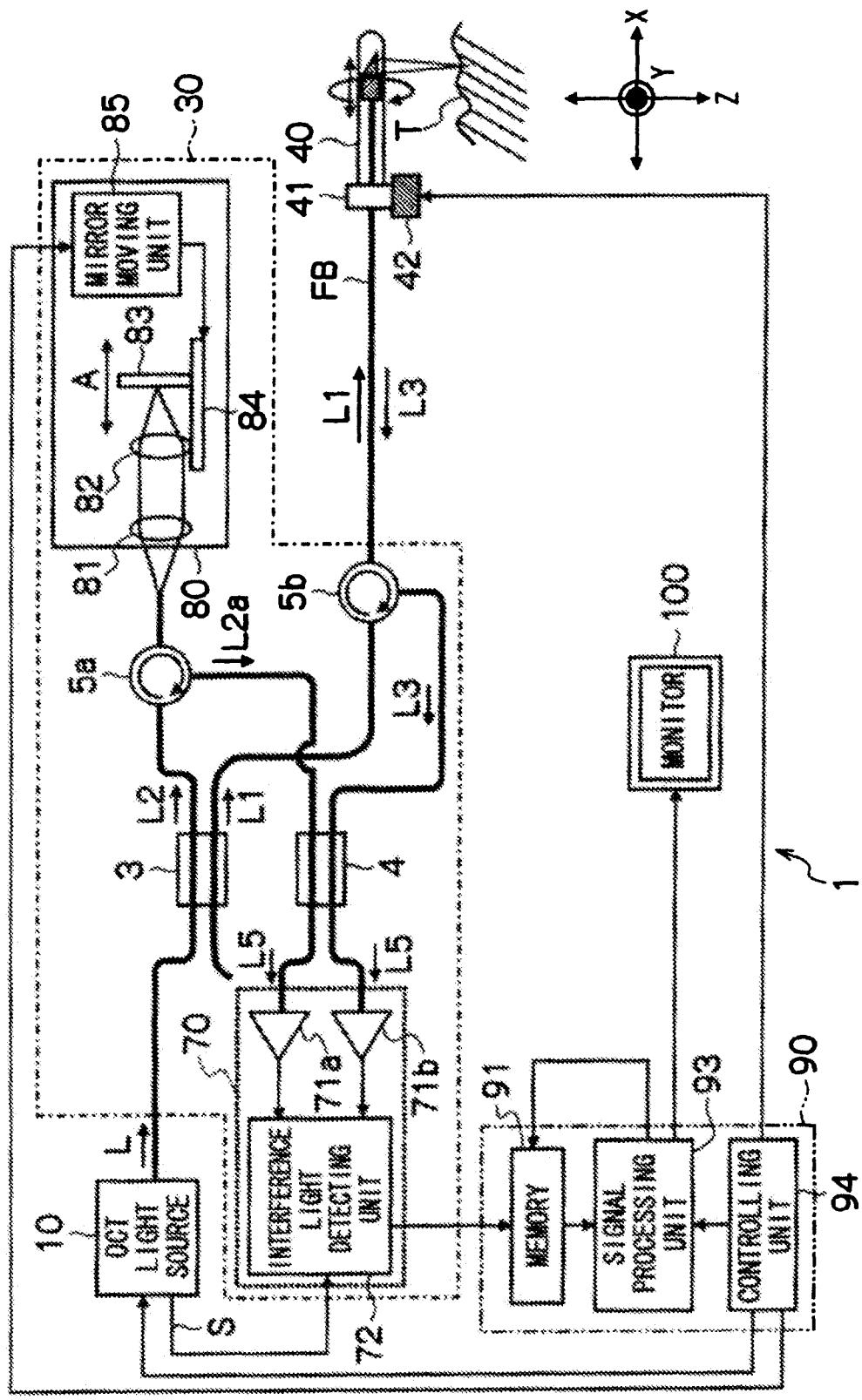
FIG. 1 is a block diagram showing a configuration of an optical three-dimensional structure imaging device according to an embodiment of the present invention.

FIG. 1 is a block diagram showing a configuration of the optical three-dimensional structure imaging device according to the embodiment of the present invention. As shown in FIG. 1, an optical three-dimensional structure imaging device 1 as an optical three-dimensional structure measuring device acquires, for example, a tomographic image of a measurement target, such as living tissues or cells in a body cavity, based on SS-OCT measurement around a wavelength of 1.3 µm. The optical three-dimensional structure measuring device includes an OCT light source 10, an OCT interferometer 30 including an interference information detecting unit 70, a probe 40, a CG image generating unit 90, and a monitor 100.

The OCT light source 10 is a light source that emits laser light L of an infrared region while sweeping the frequency at a certain period.

A light demultiplexer 3 in the OCT interferometer 30 demultiplexes the laser light L emitted from the OCT light source 10 into measurement light L1 and reference light L2. The light demultiplexer 3 is constituted by, for example, an optical coupler with a branching ratio of 90:10 and demultiplexes the light at a ratio of measurement light:reference light=90:10.

In the OCT interferometer 30, an optical path length adjusting unit 80 as reference light adjusting device adjusts the light path length of the reference light L2 demultiplexed by the light demultiplexer 3 through a circulator 5a and reflects the reference light L2.

The optical path length adjusting unit 80 changes the optical path length of the reference light L2 to adjust the position for starting the acquisition of a tomographic image and has collimator lenses 81 and 82 and a reflective mirror 83. The reference light L2 from the circulator 5a is reflected by the reflective mirror 83 after penetrating through the collimator lenses 81 and 82, and return light L2a of the reference light L2 again enters the circulator 5a through the collimator lenses 81 and 82.

The reflective mirror 83 is arranged on a movable stage 84, and a mirror moving unit 85 can move the movable stage 84 in arrow A directions. As the movable stage 84 moves in the arrow A directions, the optical path length of the reference light L2 changes. The return light L2a of the reference light L2 from the optical path length adjusting unit 80 is guided to an optical multiplexing/demultiplexing unit 4 through the circulator 5a.

Meanwhile, the measurement light L1 demultiplexed by the light demultiplexer 3 is guided to the probe 40 through a circulator 5b and an optical fiber FB. The measurement light L1 is emitted from the emission end of the probe 40 and is directed to a measurement target T. Return light L3 again enters the probe 40 and returns to the circulator 5b.

The probe 40 guides the incident measurement light L1 to the measurement target T through an optical rotary connector 41 and directs the measurement light L1 to the measurement target T. The probe 40 also guides the return light L3 from the measurement target T when the measurement light L1 is directed to the measurement target T.

Assuming that a depth direction of the measurement target T is Z, a longitudinal axis direction of the probe is X, and a direction orthogonal to a ZX plane is Y, a motor not shown in an optical scanner 42 as scanning device rotates a fiber section beyond the optical rotary connector 41 in the probe 40. As a result, the measurement light L1 is circumferentially scanned over the measurement target T, and a two-dimensional tomographic image of a ZY plane can be measured. Furthermore, a motor not shown in the optical scanner 42 causes the tip of the probe 40 to perform scanning back and forth in a direction X perpendicular to a plane formed by a scanning circle of the measurement light L1. As a result, a three-dimensional tomographic image of XYZ can be measured. The probe 40 is removably attached to the optical fiber FB through an optical connector not shown.

Figure 2:
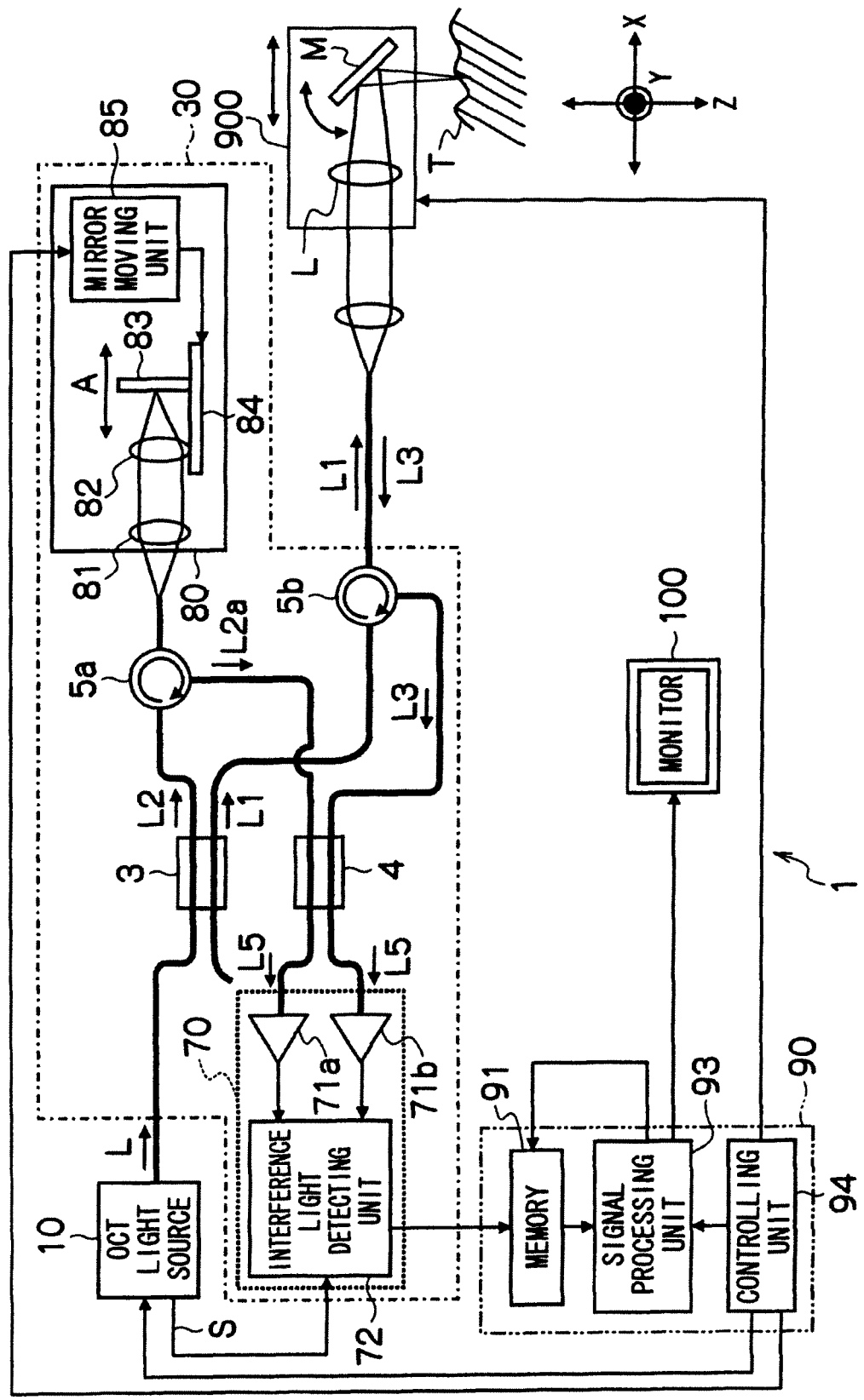
FIG. 2 is a diagram showing a modified example of scanning device in the optical three-dimensional structure imaging device of FIG. 1.

FIG. 2 is a diagram showing a modified example of the scanning device in the optical three-dimensional structure imaging device of FIG. 1.

Obviously, the shape of the probe tip and the scanning direction are not limited to these. For example, as shown in FIG. 2 near the fiber tip, a light transmitting/receiving unit 900 including a lens L and a high-speed scanning mirror M such as a galvanometer mirror may be arranged to perform two-dimensional scan by the high-speed scanning mirror M, or light collecting device and scanning device may be configured to perform scanning back and forth by a stage (not shown). Alternatively, the stage may two-dimensionally scan the measurement target. Alternatively, the optical axis scanning mechanism and the measurement sample moving mechanism may be combined. In the optical axis scanning of the OCT device, the galvanometer mirror may be used, or a type of scanning by the stage may be used. In the case of the probe, only a polarizing mirror may be rotated by the motor, or the probe may be fixed to fibers, and each fiber may rotate the probe. Other than the rotation, an MEMS (Micro Electro Mechanical Systems) mirror may be used to perform linear scanning.

The reflected light (or backscattered light) L3 from the measurement target T is guided to the OCT interferometer 30 and is guided to the optical multiplexing/demultiplexing unit 4 by the OCT interferometer 30 through the circulator 5b. The optical multiplexing/demultiplexing unit 4 multiplexes the reflected light (or backscattered light) L3 of the measurement light L1 and the return light L2a of the reference light L2 and emits the light toward the interference information detecting unit 70.

The interference information detecting unit 70 detects, at a predetermined sampling frequency, interference light L5 of the reflected light (or backscattered light) L3 of the measurement light L1 and the return light L2a of the reference light L2 multiplexed by the multiplexing/demultiplexing unit 4. The interference information detecting unit 70 includes InGaAs photodetectors 71a and 71b that measure the light intensity of the interference light L5 and an interference light detecting unit 72 that performs a balance detection of a detected value of the InGaAs photodetector 71a and a detected value of the InGaAs photodetector 71b. The interference light L5 is divided into two by the optical multiplexing/demultiplexing unit 4, is detected by the InGaAs photodetectors 71a and 71b, and is outputted to the interference light detecting unit 72. The interference light detecting unit 72 applies a Fourier transform to the interference light L5 in synchronization with a sweeping trigger signal S of the OCT light source 10 to detect the intensity of the reflected light (or backscattered light) L3 at each depth position of the measurement target T.

The CG image generating unit 90 stores, as signal intensity information of interference information, the intensity of the reflected light (or backscattered light) L3 at each depth position of the measurement target T detected by the interference light detecting unit 72 in a memory 91 as optical three-dimensional structure information storing device. The CG image generating unit 90 includes a signal processing unit 93 and a controlling unit 94 in addition to the memory 91. The signal processing unit 93 generates an optical three-dimensional structure image made of structure information of the measurement target T based on the signal intensity information of the interference information stored in the memory 91. The controlling unit 94 controls the signal processing unit 93, controls the light emission of the OCT light source 10, and controls the mirror moving unit 85.

Figure 3:
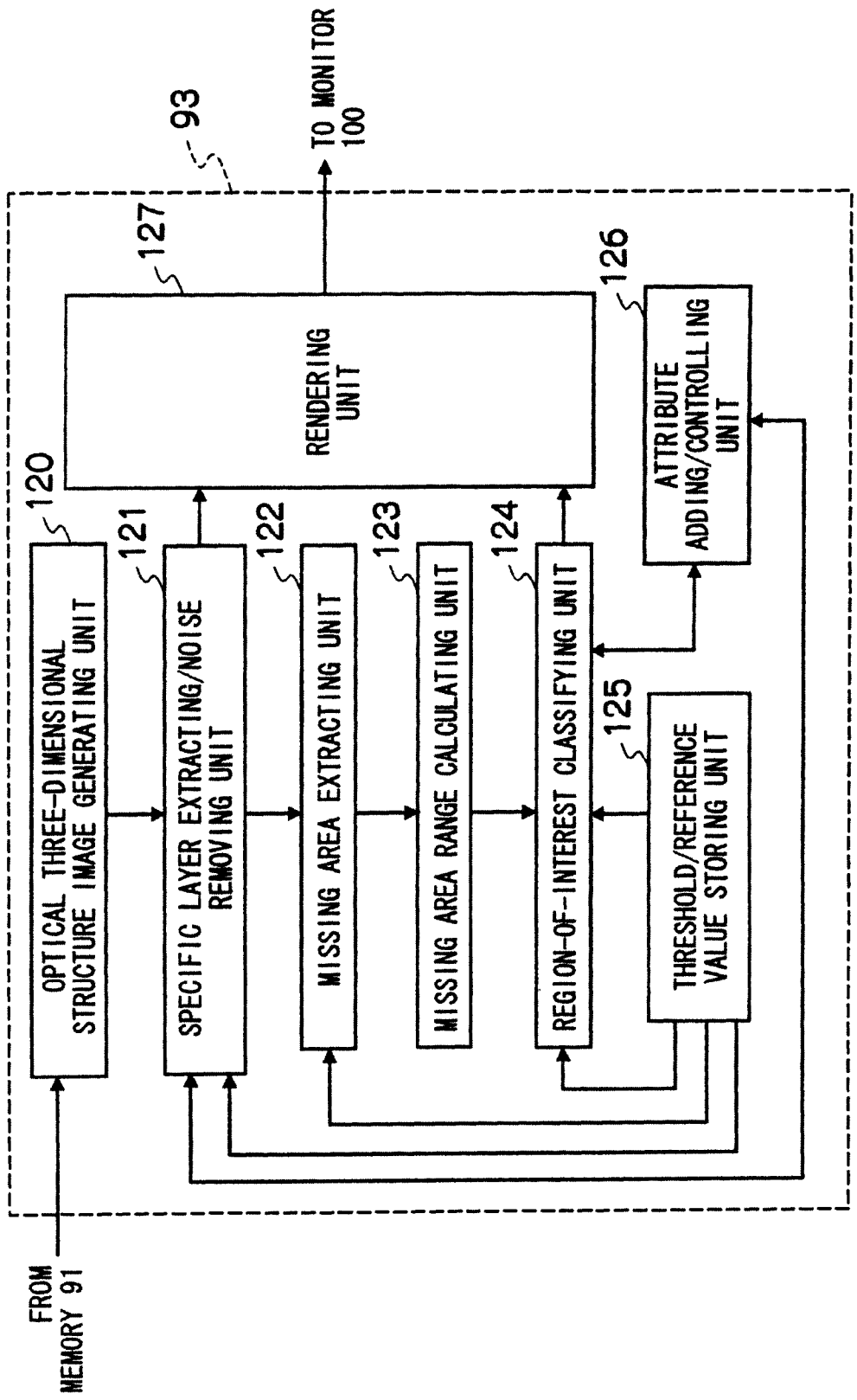
FIG. 3 is a block diagram showing a configuration of a signal processing unit of FIG. 1.

FIG. 3 is a block diagram showing a configuration of the signal processing unit of FIG. 1. As shown in FIG. 3, the signal processing unit 93 includes an optical three-dimensional structure image generating unit 120, a specific layer extracting/noise removing unit 121 as specific layer extracting device and noise area deleting device, a missing area extracting unit 122 as missing area extracting device, a missing area range calculating unit 123 as missing area range calculating device, an region-of-interest classifying unit 124 as region-of-interest classifying device, a threshold/reference value storing unit 125, an attribute adding/controlling unit 126 as attribute adding device and attribute controlling device, and a rendering unit 127 as computer graphic image building device.

The optical three-dimensional structure image generating unit 120 generates an optical three-dimensional structure image made of the structure information of the measurement target T based on the signal intensity information of the interference information stored in the memory 91.

The specific layer extracting/noise removing unit 121 compares a range of continuous structure information with a predetermined threshold to determine that an area is a specific layer area (for example, a basement membrane area or a muscularis mucosae area) of the optical three-dimensional structure image built by the optical three-dimensional structure image generating unit 120 if the range of the continuous structure information is equal to or greater than the predetermined threshold and to determine that an area is a noise area if the range of the continuous structure information is smaller than the predetermined threshold to extract the noise area of the structure information of the measurement target T to remove the noise area from the optical-dimensional structure image.

The missing area extracting unit 122 extracts missing areas in which the structure information is missing in the specific layer area extracted by the specific layer extracting/noise removing unit 121.

The missing area range calculating unit 123 calculates the size, such as the area, of the missing range extracted by the missing area extracting unit 122.

The region-of-interest classifying unit 124 compares the sizes of the missing ranges calculated by the missing area range calculating unit 123 with a predetermined range determination reference value and classifies the missing areas into a plurality of regions of interest (for example, new blood vessel areas, micro cancer invasion areas, and advanced cancer invasion areas) corresponding to the sizes of the missing ranges.

The threshold/reference value storing unit 125 stores the predetermined threshold used by the specific layer extracting/ noise removing unit 121, the range determination reference value used by the region-of-interest classifying unit 124, and the like.

The attribute adding/controlling unit 126 adds and sets attributes to the specific layer areas extracted by the specific layer extracting/noise removing unit 121 and the regions of interest classified by the region-of-interest classifying unit 124.

The rendering unit 127 applies a rendering process to the structure information of the optical three-dimensional structure image generated by the optical three-dimensional structure image generating unit 120, the specific layer areas extracted by the specific layer extracting/noise removing unit 121, and the regions of interest classified by the region-of-interest classifying unit 124 to generate a computer graphic image. Based on the attributes of the specific layer areas and the regions of interest added and set to the attribute adding/controlling unit 126, the rendering unit 127 builds the computer graphic image to allow identifying the specific layer areas and the regions of interest. Therefore, the rendering unit 127 executes, for example, different color processing or enhancement processing based on the attributes of the specific layer areas and the regions of interest to build a computer graphic image, such as an optical three-dimensional structure CG image. The rendering unit 127 is configured to output the built computer graphic image to the monitor 100.

Figure 4:
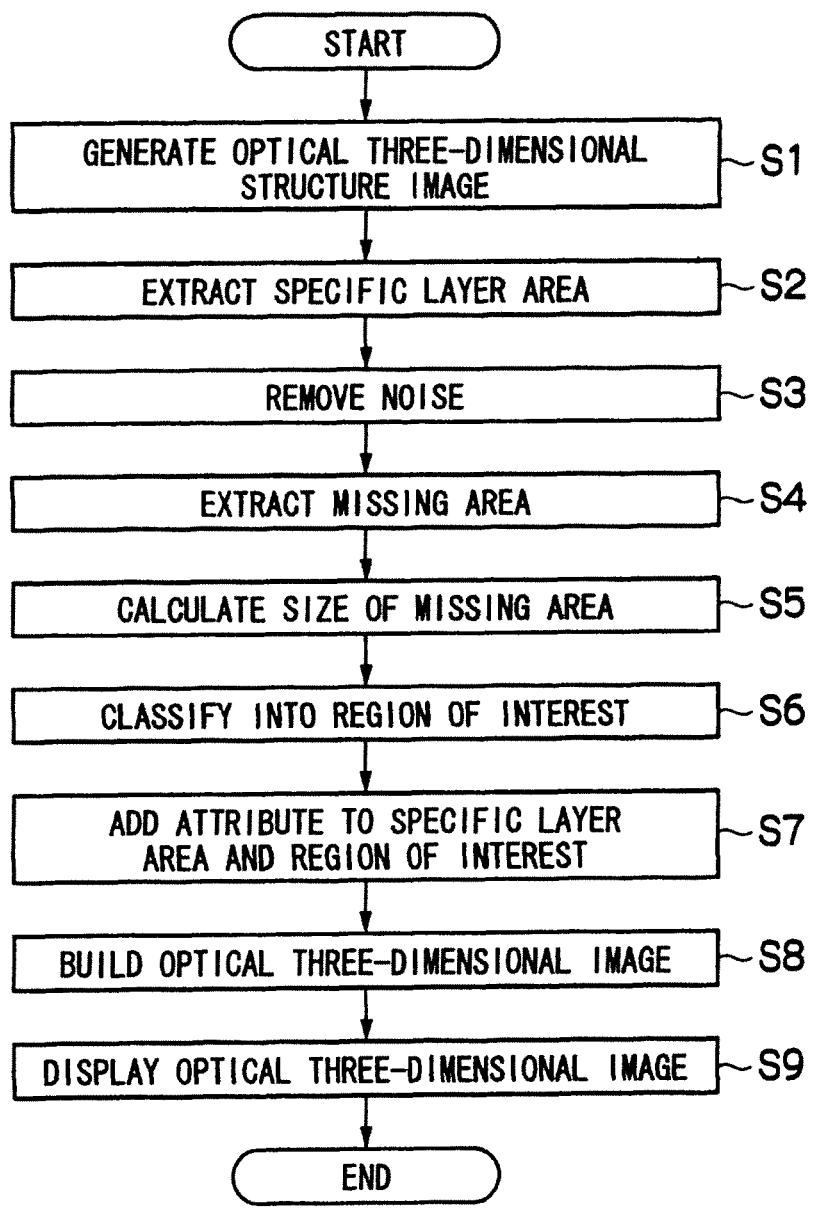
FIG. 4 is a flow chart showing a flow of a three-dimensional CG image generating process of the optical three-dimensional structure imaging device of FIG. 1.

An operation of the optical three-dimensional structure imaging device 1 of the present embodiment configured as described above will be described with reference to a flow chart of FIG. 4. FIG. 4 is a flow chart showing a flow of a three-dimensional CG image generating process of the optical three-dimensional structure imaging device of FIG. 1.

As shown in FIG. 4, the controlling unit 94 causes the optical three-dimensional structure image generating unit 120 to generate an optical three-dimensional structure image made of the structure information of the measurement target T based on the signal intensity information of the interference information stored in the memory 91 (step S1). The optical three-dimensional structure image generating unit 120 performs noise removing device, such as a low-pass filter or an averaging process, to remove high-frequency noise smaller than the size suitable for the determination of continuity.

The controlling unit 94 then causes the specific layer extracting/noise removing unit 121 to extract the structure information of the layer structure of the optical three-dimensional structure image built by the optical three-dimensional structure image generating unit 120 based on the predetermined threshold from the threshold/reference value storing unit 125 (step S2).

The controlling unit 94 further causes the specific layer extracting/noise removing unit 121 to extract noise information of the signal intensity information of the interference information of the measurement target T based on the predetermined threshold from the threshold/reference value storing unit 125 and removes the noise information from the optical three-dimensional structure image (step S3).

Figure 5:
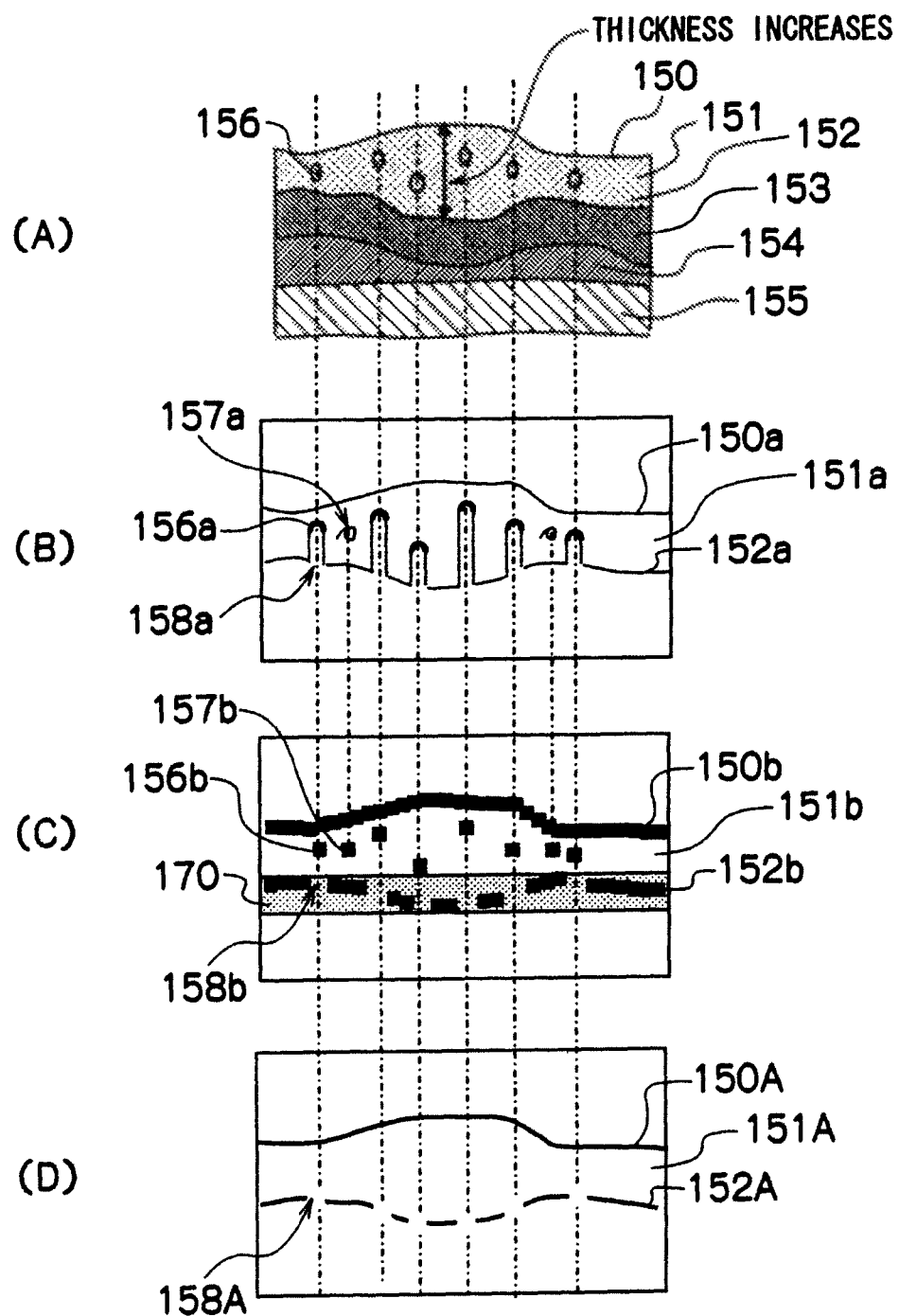
FIG. 5 is a diagram for explaining an example of a specific procedure of extracting specific layers from an optical three-dimensional structure image and removing noise of the optical three-dimensional structure image by a specific layer extracting noise removing unit of FIG. 3.
Figure 6:
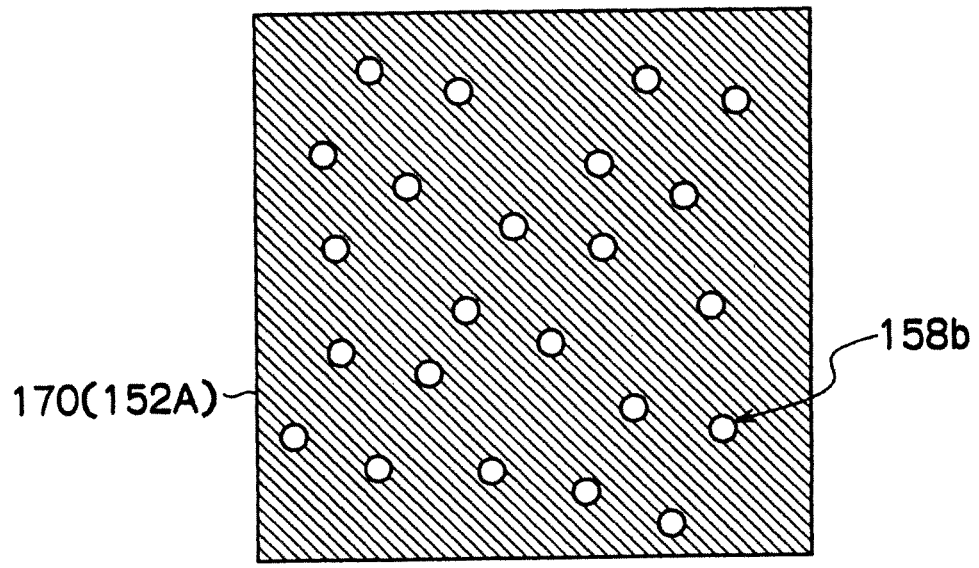
FIG. 6 is a projection diagram of the specific layers extracted by the specific layer extracting/noise removing unit of FIG. 3.

Details of the processes of steps S2 and S3 will be described with reference to FIGS. 5 to 7. FIG. 5 is a diagram for explaining an example of a specific procedure in which the specific layer extracting/noise removing unit of FIG. 3 extracts the specific layers from the optical three-dimensional structure image and removes noise of the optical three-dimensional structure image. FIG. 6 is a projection diagram of the specific layers extracted by the specific layer extracting/noise removing unit of FIG. 3.

In a section (A) of FIG. 5, esophagus in a living body has a layer structure including, for example, from the upper layer, a mucosal surface 150, a thin epithelial layer 151, a strongly scattered basement membrane 152, relatively strongly scattered lamina propria mucosae 153, relatively weakly scattered muscularis mucosae 154, a strongly scattered submucosal layer 155, and a muscular layer (not shown).

When a cancer develops on the epithelial layer 151, the thickness of the epithelial layer 151 increases, and hypertrophy is developed on the epithelial layer 151. The cancer first breaks the basement membrane 152 to invade the lamina propria mucosae 153. If the cancer further progresses, the invasion depth increases toward the muscularis mucosae 154, the submucosal layer 155, and the muscular layer. It is important to determine whether the cancer has invaded below the basement membrane 152 to distinguish the presence of the invasion of the cancer.

When the optical three-dimensional structure imaging device 1 applies OCT measurement to the mucosal tissues of the esophagus shown in the section (A) of FIG. 5, the optical three-dimensional structure imaging device 1 can obtain signal intensity information of interference information as in a section (B) of FIG. 5. To simplify the description, the section (B) of FIG. 5 schematically illustrates mucosal surface intensity information 150a, epithelial layer intensity information 151a, and basement membrane intensity information 152a as the signal intensity information of the interference information of the mucosal surface 150, the epithelial layer 151, and the basement membrane 152 at a cross section with a depth direction of the lamination of the esophagus.

Since there are, for example, capillaries 156 in the epithelial layer 151 as shown in the section (A) of FIG. 5, capillary intensity information 156a corresponding to the capillaries 156 is detected in the epithelial layer intensity information 151a as shown in the section (B) of FIG. 5. The capillary intensity information 156a is shadowed relative to the lower layer during the OCT measurement, and missing sections 158a without the intensity information are generated in the basement membrane intensity information 152a. A noise component 157a may be further generated in the epithelial layer intensity information 151a.

Therefore, the specific layer extracting/noise removing unit 121 extracts mucosal surface structure information 150b, epithelial layer structure information 151b, and basement membrane structure information 152b as the structure information of the mucosal surface 150, the epithelial layer 151, and the basement membrane 152 from the signal intensity information of the interference information in step S2.

When the structure information is extracted, structure information 156b and 157b of small areas caused by the capillaries or noise is extracted in the epithelial layer structure information 151b as shown in a section (C) of FIG. 5, and missing areas 158b without information shadowed by the capillaries and the like are extracted in the basement membrane structure information 152b.

In step S2, the specific layer extracting/noise removing unit 121 compares the size of the range of continuous structure information (length of the continuous structure information in the case of the section (C) of FIG. 5) with the predetermined threshold stored in the threshold/reference value storing unit 125 and extracts the mucosal surface 150, the epithelial layer 151, and the basement membrane 152 that are the specific layer areas of the optical three-dimensional structure image built by the optical three-dimensional structure image generating unit 120 if the size of the range of the continuous structure information is equal to or greater than the predetermined threshold. The missing areas 158b are extracted along with the epithelial layer 151.

In step S3, the specific layer extracting/noise removing unit 121 further determines that the areas are noise areas if the size of the range of the continuous structure information is smaller than the predetermined threshold and extracts the noise areas of the structure information of the measurement target T. The specific layer extracting/noise removing unit 121 then removes the noise areas from the optical three-dimensional structure image. Therefore, the specific layer extracting/noise removing unit 121 removes the structure information 156b and 157b of the small areas shown in the section (C) of FIG. 5 as the noise areas from the optical three-dimensional structure image in the process of step S3.

As a result of the processes of steps S2 and S3, the specific layer extracting/noise removing unit 121 extracts a mucosal surface area 150A, an epithelial layer area 151A, and a basement membrane area 152A that are made of the structure information 156b and 157b and from which the noise areas are removed as shown in a section (D) of FIG. 5. Missing areas 158A are extracted along with the epithelial layer area 151A.

Although two-dimensional cross-sectional images are used and described in FIG. 5 for the simplification of the description, the specific layer extracting/noise removing unit 121 specifically applies the processes of steps S2 and S3 to the entire optical three-dimensional structure image.

More specifically, the specific layer extracting/noise removing unit 121 first extracts points (extraction points) where the signal intensity information of the interference information is high in the depth direction. This is applied to the entire three-dimensional image.

Adjacent extraction points are integrated to form some extraction areas. In each extraction area, the specific layer extracting/noise removing unit 121 separates continuous layers (for example, the mucosal surface area 150A, the epithelial layer area 151A, and the basement membrane area 152A) and the other structures (for example, the structure information 156b and 157b: see the section (C) of FIG. 5).

In each extraction area, the specific layer extracting/noise removing unit 121 determines that the layers are continuous layers (for example, the mucosal surface area 150A, the epithelial layer area 151A, and the basement membrane area 152A) if the area of a projection diagram 170 (the size of the range of the continuous structure information) is equal to or greater than a certain area (the predetermined threshold stored in the threshold/reference value storing unit 125) in the projection diagram 170 as seen from the upper surface shown in FIG. 6 and assumes that the areas are noise areas in the other cases (for example, the structure information 156b and 157b: see the section (C) of FIG. 5) to remove the noise areas.

Returning to FIG. 4, the controlling unit 94 causes the missing area extracting unit 122 to extract the plurality of missing areas 158A generated on the projection diagram 170 of the basement membrane area 152A shown for example in FIG. 6 (step S4).

The controlling unit 94 causes the missing area range calculating unit 123 to calculate the sizes, such as areas, of the missing areas 158A extracted by the missing area extracting unit 122 (step S5).

The controlling unit 94 causes the region-of-interest classifying unit 124 to compare the sizes of the missing areas 158A calculated by the missing area range calculating unit 123 with the predetermined range determination reference value from the threshold/reference value storing unit 125 and classify the missing areas 158A into a plurality of regions of interest (for example, new blood vessel areas, micro cancer invasion areas, and advanced cancer invasion areas) corresponding to the sizes of the missing ranges (step S6).

Specifically, the region-of-interest classifying unit 124 classifies the missing areas 158A in the projection diagram 17 into regions of interest of classes corresponding to, for example, the diameters. For example, the region-of-interest classifying unit 124 classifies the missing areas 158A into regions of interest A if the diameter is less than 10 microns (for example, normal capillary areas or noise), regions of interest B if the diameter is 10 microns or more and less than 200 microns (for example, new blood vessel areas), regions of interest C if the diameter is 200 microns or more and less than 1 mm (for example, micro invasion areas), and regions of interest D if the diameter is 1 mm or more (for example, advanced invasion areas).

The controlling unit 94 causes the attribute adding/controlling unit 126 to add and set attributes to the specific layer areas (the mucosal surface area 150A, the epithelial layer area 151A, and the basement membrane area 152A) extracted by the specific layer extracting/noise removing unit 121 and to the regions of interest classified by the region-of-interest classifying unit 124 (step S7). For example, color attributes are added and set to the specific layer areas and the regions of interest.

The controlling unit 94 causes the rendering unit 127 to apply a rendering process to the optical three-dimensional structure image generated by the optical three-dimensional structure image generating unit 120 and the structure information of the specific layer areas extracted by the specific layer extracting/noise removing unit 121 and the regions of interest classified by the region-of-interest classifying unit 124 to generate a computer graphic image (step S8). The rendering unit 127 builds the computer graphic image based on the attributes of the specific layer areas and the regions of interest added and set by the attribute adding/controlling unit 126 to allow identifying the specific layer areas and the regions of interest. More specifically, the rendering unit 127 executes, for example, different color processing or enhancement processing based on the attributes of the specific layer areas and the regions of interest to build the computer graphic image.

The controlling unit 94 outputs the computer graphic image built by the rendering unit 127 to the monitor 100 and displays the computer graphic image on the monitor 100 (step S9).

The processes of steps S6 to S8 will be specifically described in first and subsequent examples.

FIRST EXAMPLE

Figure 7:
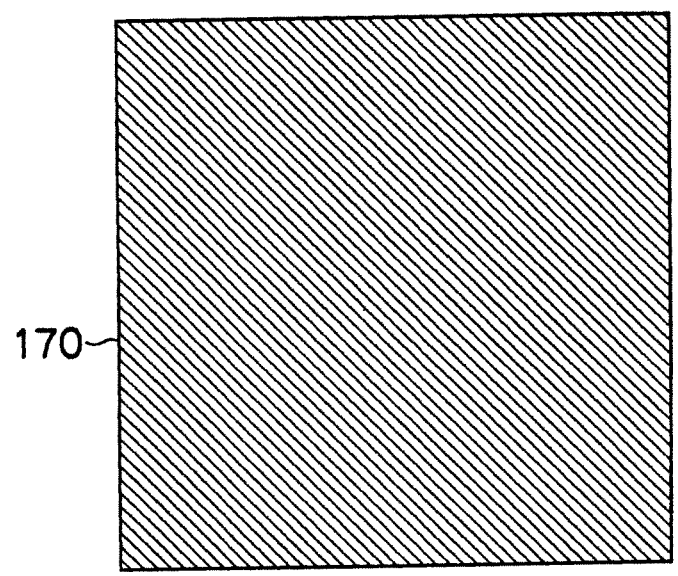
FIG. 7 is a diagram explaining deletion of regions of interest A from the specific layers by an attribute adding/controlling unit of FIG. 3 according to a first example.
Figure 8:
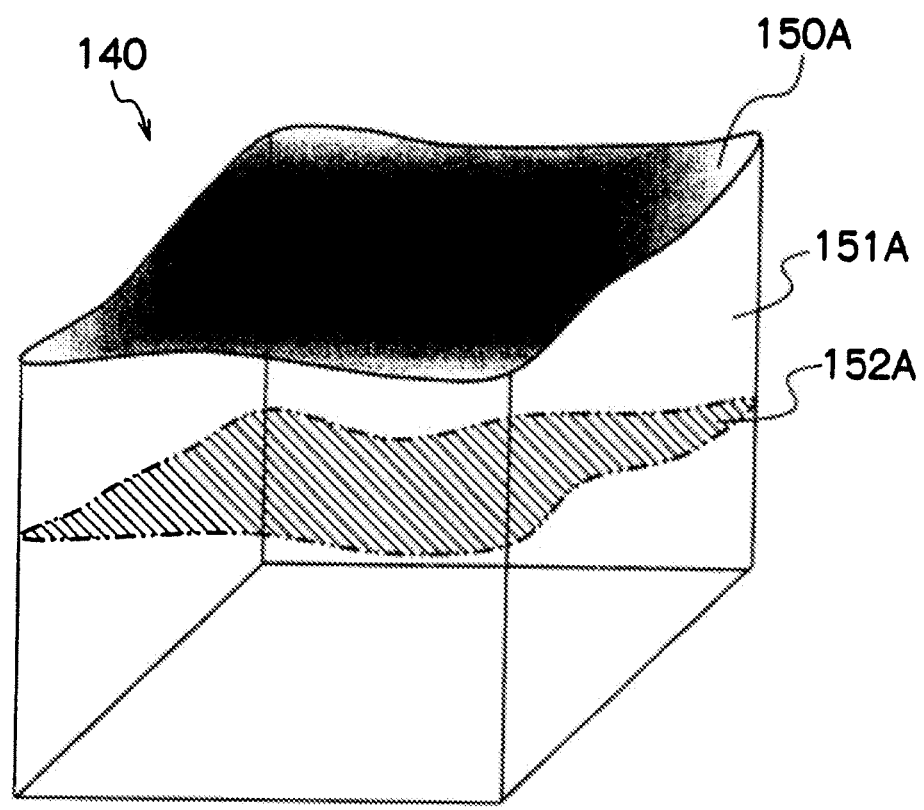
FIG. 8 is a diagram showing an example of a computer graphic image generated by a rendering unit of FIG. 3 according to the first example.

FIG. 7 is a diagram explaining deletion of the regions of interest A from the specific layers by the attribute adding/controlling unit of FIG. 3 according to a first example. FIG. 8 is a diagram showing an example of a computer graphic image generated by the rendering unit of FIG. 3 according to the first example.

In the case of the missing areas 158b in the basement membrane area 152A described in FIGS. 5 and 6, the region-of-interest classifying unit 124 classifies the missing areas 158b into, for example, the regions of interest A (for example, normal capillary areas or noise) in step S6 if the areas are smaller than 10 microns.

The attribute adding/controlling unit 126 adds the same attribute as that of the basement membrane area 152A to the regions of interest A in step S7 to delete the regions of interest A (missing areas 158b) from the basement membrane area 152A as shown in FIG. 7.

In this way, the rendering unit 127 renders the specific layer areas (the mucosal surface area 150A, the epithelial layer area 151A, and the basement membrane area 152A) including the color attributes added to the optical three-dimensional structure image generated by the optical three-dimensional structure image generating unit 120 to generate a computer graphic image 140 in step S8 as shown in FIG. 8. In the computer graphic image 140, the missing areas 158 are deleted from the basement membrane area 152A.

SECOND EXAMPLE

Figure 9:
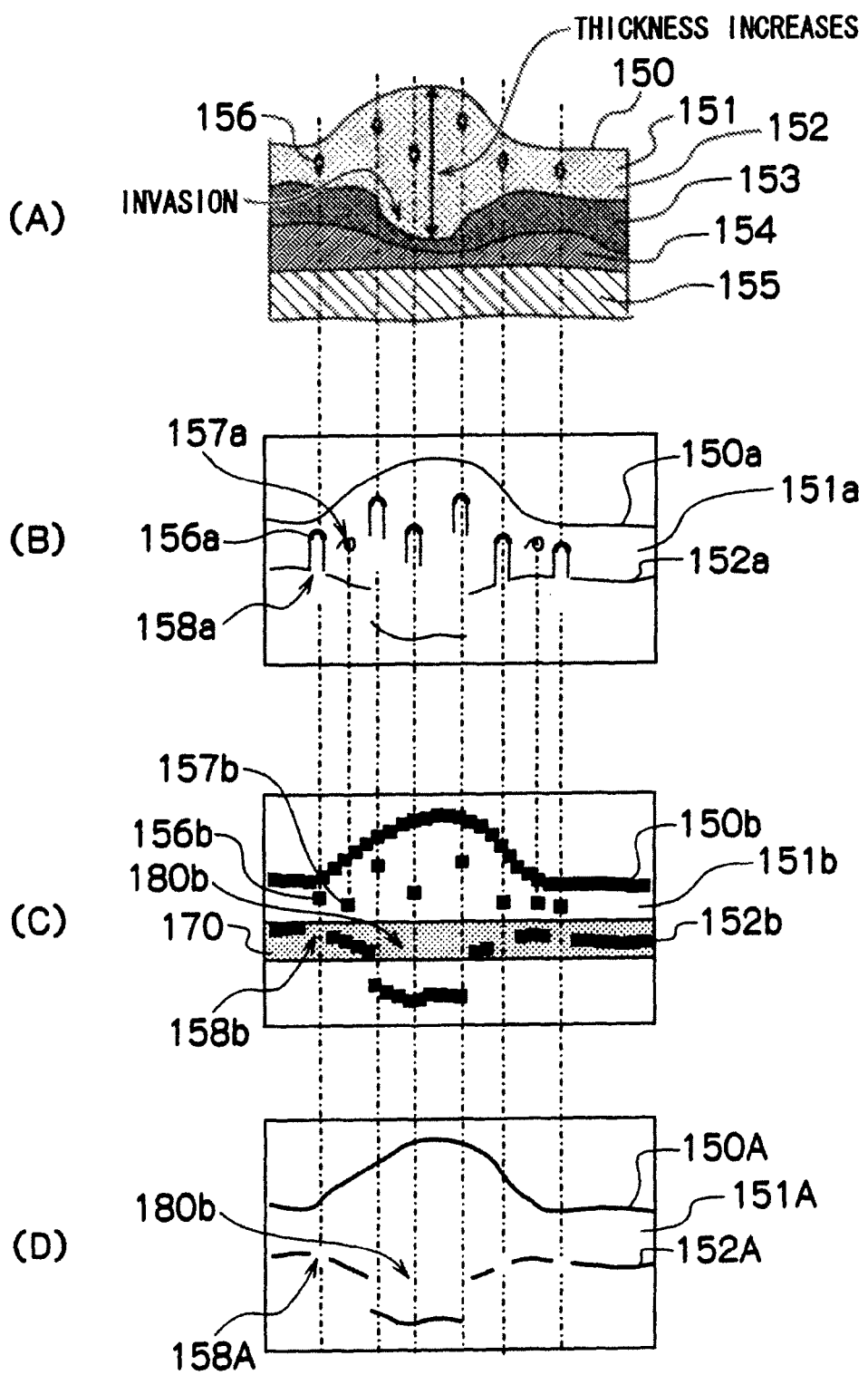
FIG. 9 is a diagram for explaining a second example of the procedure of FIG. 5.
Figure 10:
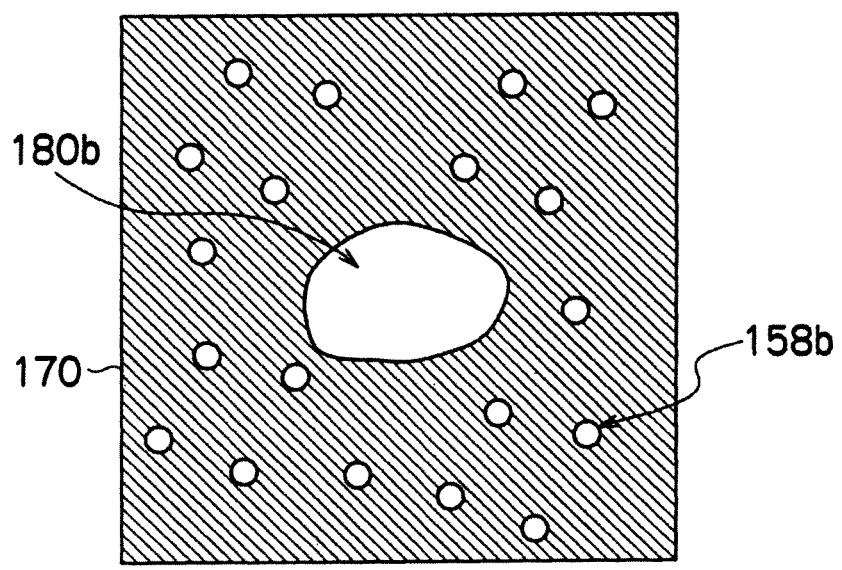
FIG. 10 is a projection diagram of the specific layers according to the second example extracted by the specific layer extracting/noise removing unit of FIG. 3.
Figure 11:
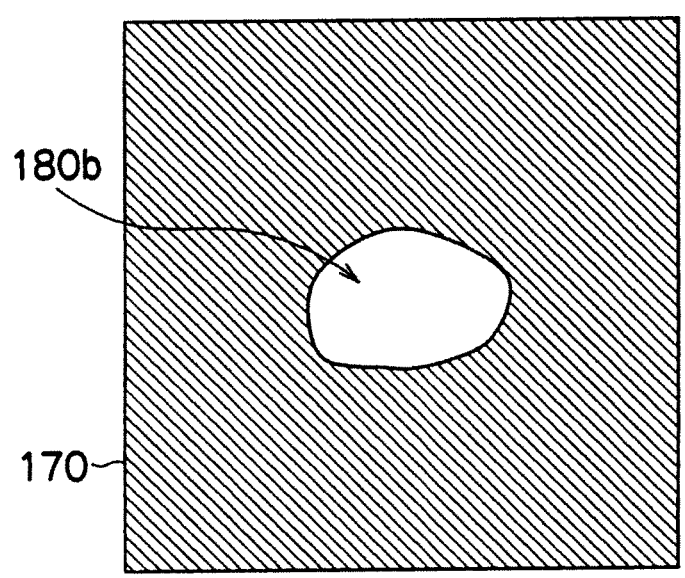
FIG. 11 is a diagram explaining processing according to the second example of the regions of interest in the specific layers by the attribute adding/controlling unit of FIG. 3.
Figure 12:
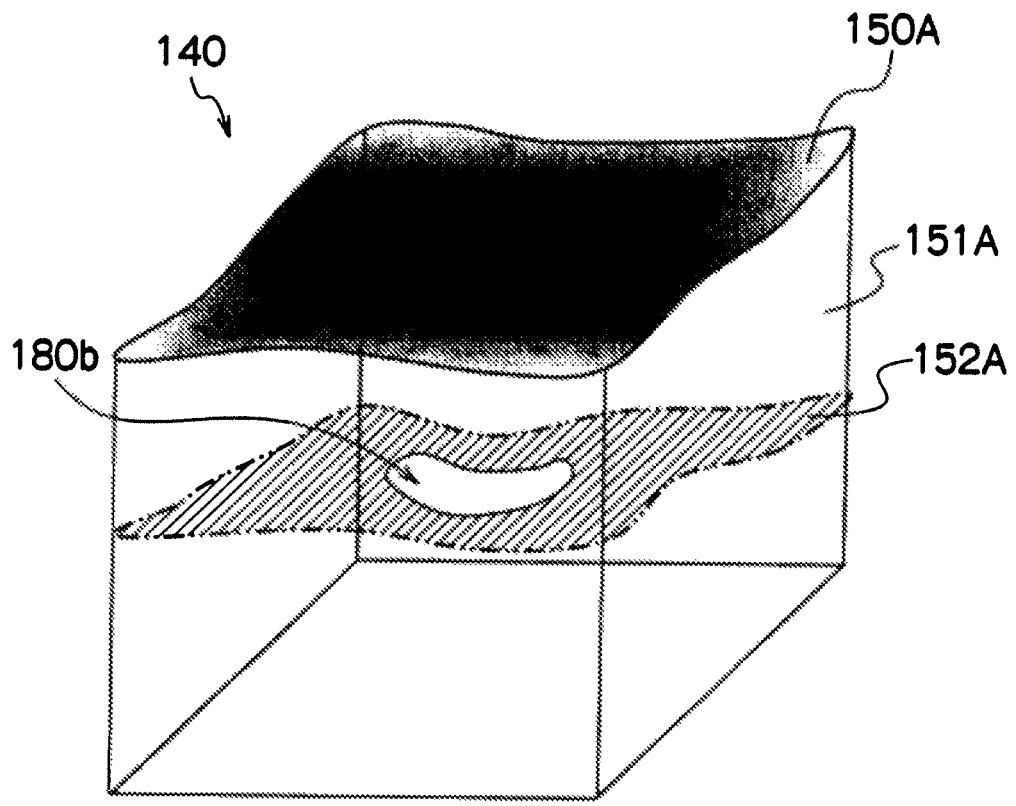
FIG. 12 is a diagram showing an example of the computer graphic image according to the second example generated by the rendering unit of FIG. 3.

FIG. 9 is a diagram for explaining a second example of the procedure of FIG. 5. FIG. 10 is a projection diagram of the specific layers according to the second example extracted by the specific layer extracting/noise removing unit of FIG. 3. FIG. 11 is a diagram explaining processing according to the second example of the regions of interest in the specific layers by the attribute adding/controlling unit of FIG. 3. FIG. 12 is a diagram showing an example of the computer graphic image according to the second example generated by the rendering unit of FIG. 3. The processing content in sections (A) to (D) of FIG. 9 is the same as the processing content in the sections (A) to (D) of FIG. 5, and the description will not be repeated.

As shown in FIG. 9, when the cancer invades the basement membrane area 152A and part of the basement membrane area 152A is lost, the region-of-interest classifying unit 124 classifies in step S6 a missing area 180b caused by the loss into the region of interest D (for example, advanced invasion areas) if the diameter is, for example, 1 mm or more. The region-of-interest classifying unit 124 classifies the missing areas 158b in the sections (A) to (D) of FIG. 9 into the regions of interest A (for example, normal capillary areas or noise) as in the first example if the diameter is, for example, less than 10 microns.

In each extraction area, the specific layer extracting/noise removing unit 121 determines that the layers are continuous layers (for example, the mucosal surface area 150A, the epithelial layer area 151A, and the basement membrane area 152A) if the area (the size of the range of the continuous structure information) of the projection diagram 170 is equal to or greater than a certain area (the predetermined threshold stored in the threshold/reference value storing unit 125) in the projection diagram 170 as seen from the upper surface shown in FIG. 10 and assumes that the area is a noise area in the other cases (for example, the structure information 156b and 157b) to remove the area.

The attribute adding/controlling unit 126 adds the same attribute as that of the basement membrane area 152A to the regions of interest A in the projection diagram 170 to delete the regions of interest A (the missing areas 158) from the basement membrane area 152A as shown in FIG. 11 and leaves the missing area 180b on the basement membrane area 152A as the region of interest D (advanced invasion area) with a diameter of 1 mm or more (step S7).

In this way, the rendering unit 127 renders the specific layer areas (the mucosal surface area 150A, the epithelial layer area 151A, and the basement membrane area 152A), in which, for example, identifiable color attributes are added to the optical three-dimensional structure image generated by the optical three-dimensional structure image generating unit 120 to generate the computer graphic image 140 in step S8 as shown in FIG. 12. In the computer graphic image 140, the missing areas 158 are deleted from the basement membrane area 152A, and an advanced invasion area as the region of interest D (the missing area 180b) provided with, for example, an identifiable color attribute is rendered in the basement membrane area 152A.

THIRD EXAMPLE

Figure 13:
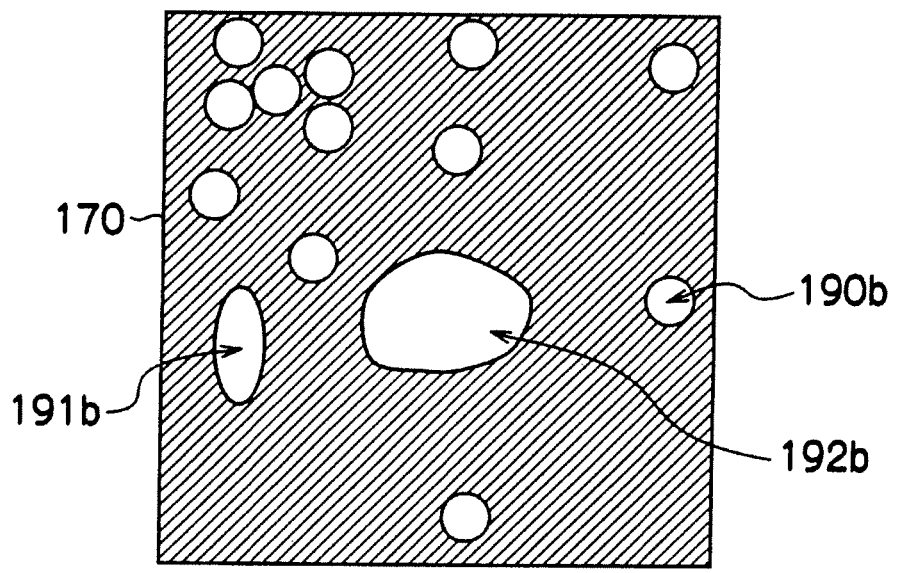
FIG. 13 is a projection diagram of the specific layers according to a third example extracted by the specific layer extracting/noise removing unit of FIG. 3.
Figure 14:
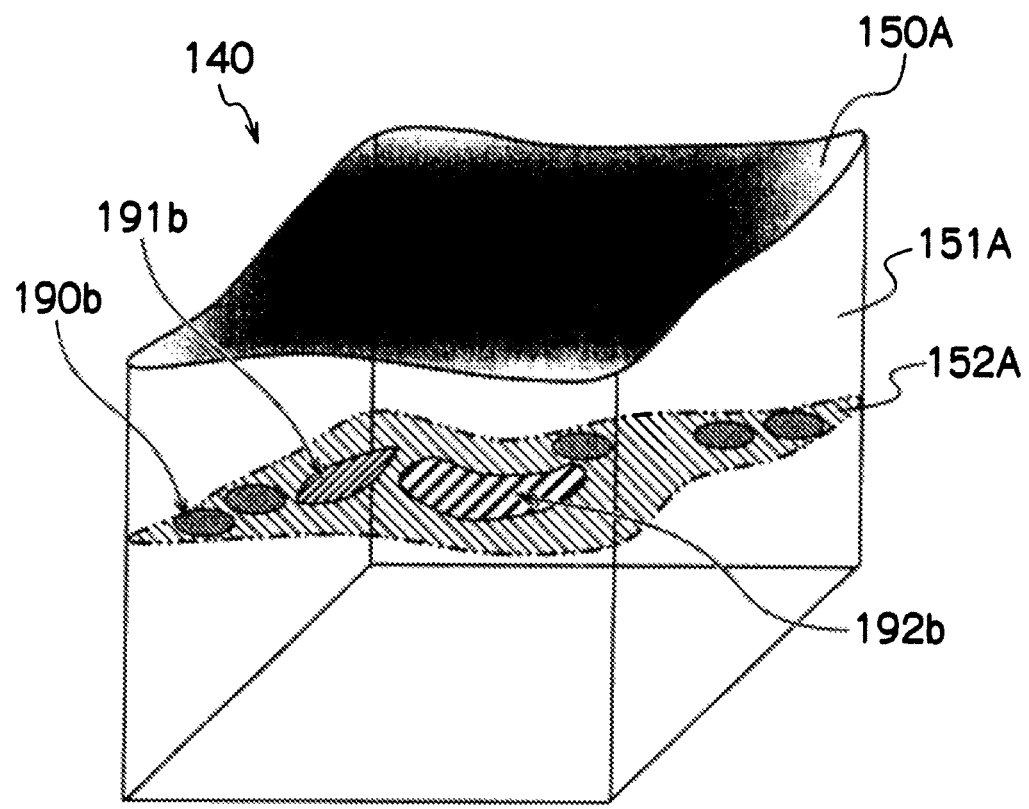
FIG. 14 is a diagram showing an example of the computer graphic image according to a third example generated by the rendering unit of FIG. 3.

FIG. 13 is a projection diagram of specific layers according to a third example extracted by the specific layer extracting/noise removing unit of FIG. 3. FIG. 14 is a diagram showing an example of the computer graphic image according to the third example generated by the rendering unit of FIG. 3.

In the case of early-stage cancer of esophagus, new blood vessels pass through the submucosal layer and the basement membrane to extend to the mucosal epithelial layer to form an IPCL (intra-epithelial papillary capillary loop). If the cancer progresses, the cancer breaks the basement membrane and enters the submucosal layer. The new blood vessels are formed in random directions toward the cancer. In normal endoscopy, a method of determining the grade of cancer from the density distribution and the shapes of the new blood vessels that can be seen through from the surface is implemented. However, only the new blood vessels approaching the mucosal surface are observed.

The third example is an example for determining the distribution of the new blood vessels inside a living body and observing the state of the basement membrane based on the new blood vessels.

The region-of-interest classifying unit 124 classifies the missing areas into, for example, the regions of interest A to D in step S6.

The attribute adding/controlling unit 126 adds the same attribute as that of the basement membrane area 152A to the regions of interest A in the projection diagram 170 to delete the regions of interest A (the missing areas 158) from the basement membrane area 152A as shown in FIG. 13 and leaves missing areas 190b as the regions of interest B (new blood vessel areas) with diameters of 10 microns or more and less than 200 microns, a missing area 191b as the region of interest C (micro invasion area) with a diameter of 200 microns or more and less than 1 mm, and a missing area 192b as the region of interest D (advanced invasion area) with a diameter of 1 mm or more on the basement membrane area 152A (step S7).

In this way, the rendering unit 127 renders the specific layer areas (the mucosal surface area 150A, the epithelial layer area 151A, and the basement membrane area 152A) including, for example, identifiable color attributes added to the optical three-dimensional structure image generated by the optical three-dimensional structure image generating unit 120 to generate the computer graphic image 140 in step S8 as shown in FIG. 14. In the computer graphic image 140, the missing areas 158 are deleted from the basement membrane area 152A, and the new blood vessel areas, the micro invasion area, and the advanced invasion area as the regions of interest B to D (the missing areas 190b, the missing area 191b, and the missing area 192b) provided with, for example, identifiable color attributes in the basement membrane area 152A are rendered.

Figure 15:
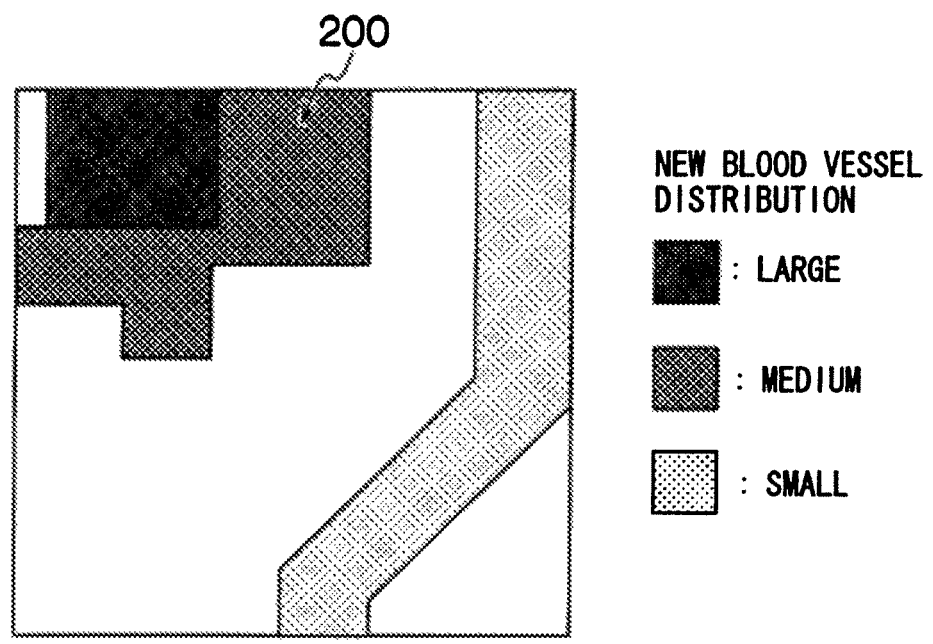
FIG. 15 is a diagram showing a distribution image of new blood vessels generated by the attribute adding/controlling unit of FIG. 3.
Figure 16:
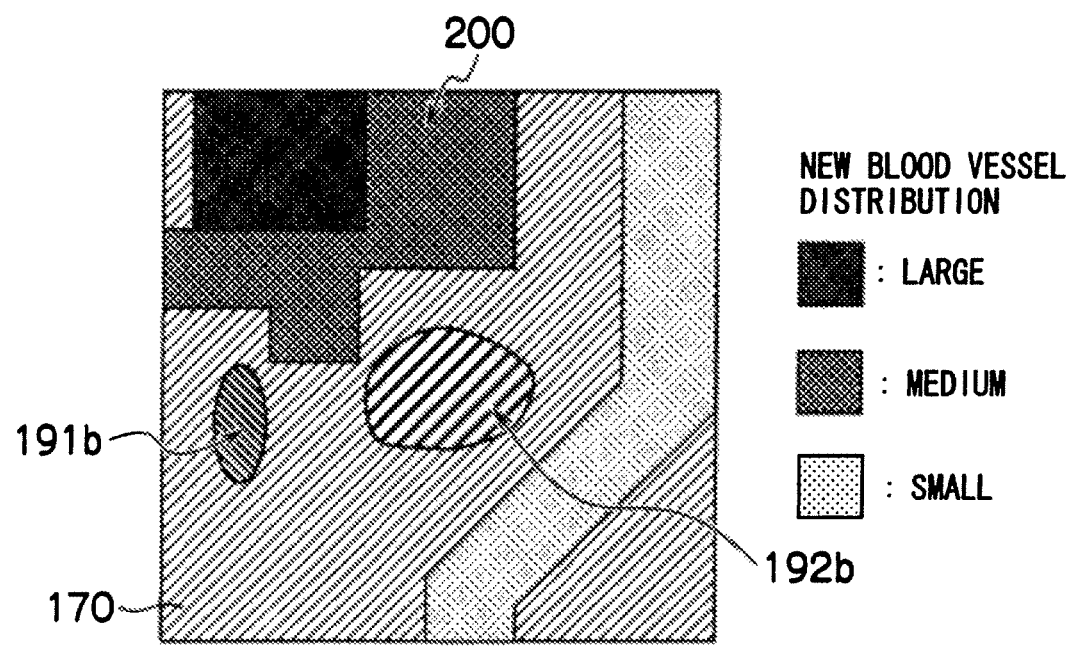
FIG. 16 is a diagram when the distribution image of new blood vessels of FIG. 15 is superimposed on a basement membrane area.
Figure 17:
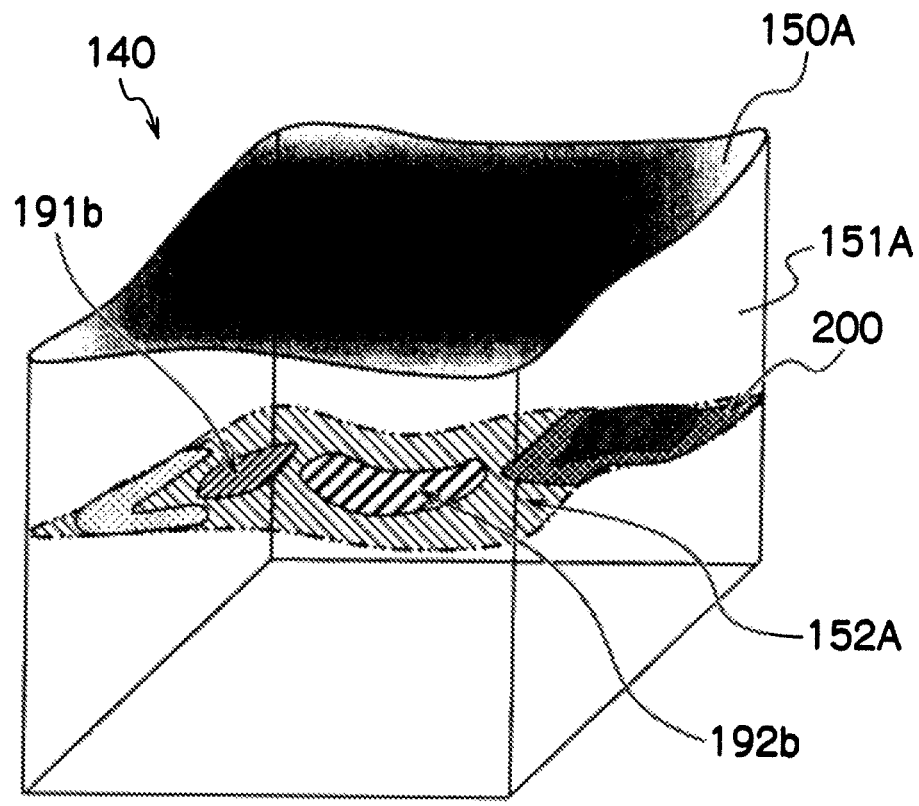
FIG. 17 is a diagram showing the computer graphic image created by rendering the distribution image of new blood vessels of FIG. 15.

FIG. 15 is a diagram showing a distribution image of new blood vessels generated by the attribute adding/controlling unit of FIG. 3. FIG. 16 is a diagram when the distribution image of the new blood vessels of FIG. 15 is superimposed on the basement membrane area. FIG. 17 is a diagram showing a computer graphic image rendering the distribution image of the new blood vessels of FIG. 15.

The attribute adding/controlling unit 126 of the third example generates a distribution of new blood vessels as a distribution image 200 as shown in FIG. 15 and can superimpose the distribution image 200 of the new blood vessels on the projection diagram 170 of the basement membrane area 152A as shown in FIG. 16. As a result, the rendering unit 127 can generate the computer graphic image 140 as shown in FIG. 17 that allows easily recognizing the distribution state of the new blood vessels in the basement membrane, and the cancer can be more surely diagnosed.

In the third example, the density of new blood vessels and the state of invasion can be particularly displayed in an easily understood manner based on the structure of the basement membrane. A layer structure is more surely extracted even in an unclear area at a deep section caused by a structure at a shallow area. The third example is also effective in the diagnosis of age-related macular degeneration, diabetic retinopathy, retinal vein occlusion, and neovascular glaucoma that cause intraocular new blood vessels. In this case, retina is extracted and observed instead of the basement membrane.

As described in the present embodiment and the first to third embodiments, the following advantageous effects can be particularly obtained.

(1) A specific layer can be easily extracted even if a living structure is changed by a lesion.

(2) A layer structure can be more surely extracted even in an unclear area at a deep section caused by a structure in a shallow area.

(3) A loss of continuity of layer structures caused by cancer can be easily determined.

According to the present embodiment, the continuity of layer areas can be easily identified from structure information of a measurement target with a layer structure, and structure information of an unclear layer area at a deep section caused by a structure in a shallow layer area can be surely extracted.

Figure 18:
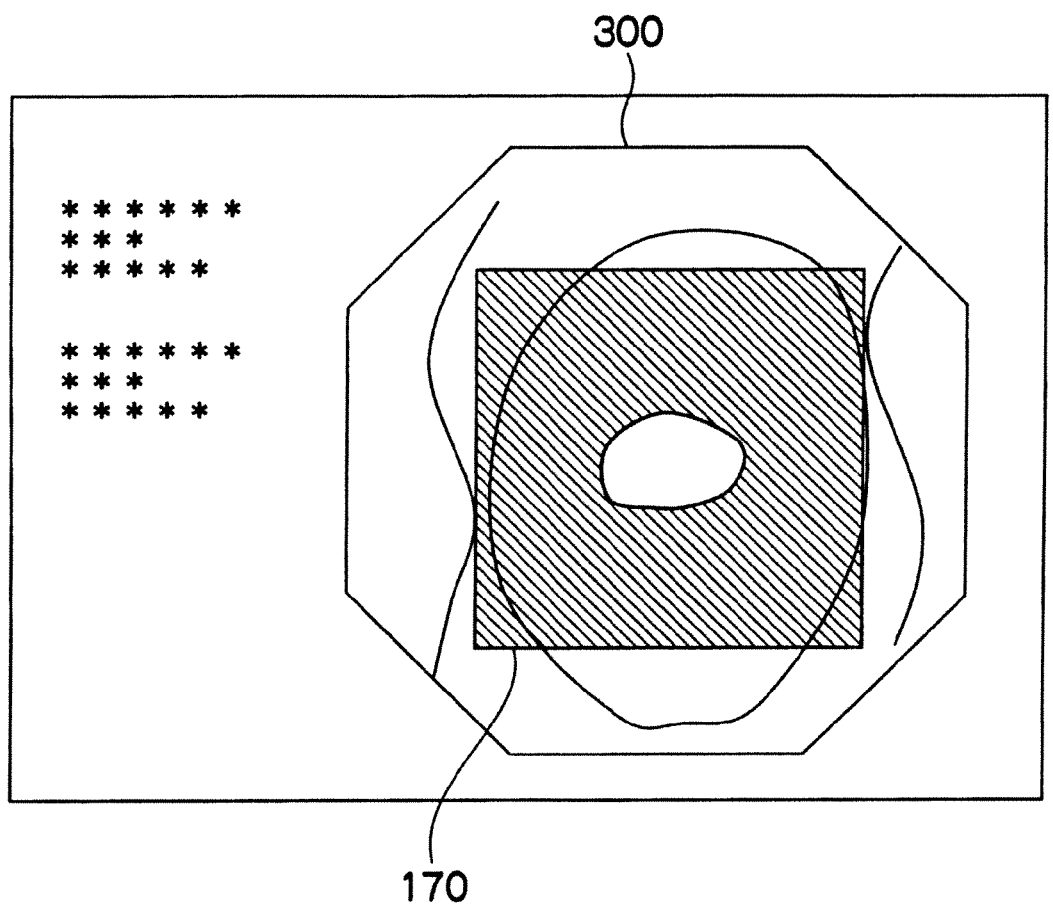
FIG. 18 is a diagram superimposing the projection diagram of FIG. 11 on an endoscopic image.

FIG. 18 is a diagram superimposing the projection diagram of FIG. 11 on an endoscopic image. When the probe 40 is inserted to a clamp channel of an endoscope to perform endoscopic image observation and OCT measurement in the present embodiment and the first to third embodiments, the rendering unit 127 can superimpose the projection diagram 170 on an endoscopic image 300 in a translucent state as shown in FIG. 18. The rendering unit 127 can display, on the monitor 100, an image formed by superimposing the projection diagram 170 on the endoscopic image 300 in a translucent state to improve the diagnosis of cancer.

Examples of methods of cancer screening include a known method called NBI (Narrow Band Imaging) and a known method called FICE (Flexible spectral Imaging Color Enhancement). These are methods for imaging blue and green wavelength regions to facilitate viewing the features of the lesion. An image formed by superimposing the projection diagram 170 on an NBI/FICE image in a translucent state may be displayed on the monitor 100.

Although the optical three-dimensional structure measuring device of the present invention has been described in detail, the present invention is not limited to the examples, and it is obvious that various modifications and changes can be made without departing from the scope of the present invention.

Although an example of the basement membrane of esophagus has been described, the invasion can be viewed in an easily understood manner if muscularis mucosae is extracted in other digestive tracts, such as stomach, small intestine, and large intestine. The present invention can also be applied to tissues if a specific membrane or a layer structure is abnormally changed in the tissues, such as digestive tracts including oral cavity, tongue, pharynx, stomach, small intestine, large intestine, and bile duct that have basement membranes, respiratory organs including nasal cavity, larynx, and bronchi, urinary organs including bladder, ureter, and urethra, genital organs including womb and vagina, skin, and ocular fundus with a layer structure.

REFERENCE SIGNS LIST

1 . . . optical three-dimensional structure imaging device, 10 . . . OCT light source, 30 . . . OCT interferometer, 40 . . . probe, 70 . . . interference information detecting unit, 90 . . . CG image generating unit, 91 . . . memory, 93 . . . signal processing unit, 94 . . . controlling unit, 100 . . . monitor, 120 . . . optical three-dimensional structure image generating unit, 121 . . . specific layer extracting/noise removing unit, 122 . . . missing area extracting unit, 123 . . . missing area range calculating unit, 124 . . . region-of-interest classifying unit, 125 . . . threshold/reference value storing unit, 126 . . . attribute adding/controlling unit, 127 . . . rendering unit

The invention claimed is:

1. An optical three-dimensional structure measuring device that directs measurement light in a depth direction of a lamination of a measurement target with a layer structure and that two-dimensionally scans an optical axis of the measurement light to acquire optical three-dimensional structure information of the measurement target, the optical three-dimensional structure measuring device comprising:

an optical three-dimensional structure information storing device for storing the optical three-dimensional structure information;

a specific layer extracting device for comparing information values of the optical three-dimensional structure information stored in the optical three-dimensional structure information storing device with a predetermined threshold and extracting, as a specific layer area of the measurement target, an area equal to or greater than a predetermined range where the information values of the optical three-dimensional structure information equal to or greater than the predetermined threshold continue;

a missing area extracting device for extracting, as missing areas, areas where the information values of the optical three-dimensional structure information are smaller than the predetermined threshold in the specific layer area;

a missing area range calculating device for calculating sizes of ranges of the missing areas; and a region-of-interest classifying device for comparing the sizes of the ranges of the missing areas with a plurality of predetermined range determination reference values, and classifying the missing areas into a plurality of types of regions of interest of classes corresponding to the sizes of the ranges of the missing areas, wherein the region-of-interest classifying device compares the sizes of the ranges of the missing areas with a first range determination reference value and a second range determination reference value which are among the predetermined range determination reference values, and the optical three-dimensional structure measuring device further comprising:

an attribute adding device for adding the same attribute as the specific layer area to the missing area whose size is less than the first range determination reference value to delete the missing area, and for adding a different attribute from the specific layer area to the missing area whose size is the second range determination reference value or more.

2. The optical three-dimensional structure measuring device according to claim 1, wherein the specific layer extracting device comprises a noise area deleting device for determining an area as a noise area to delete the area from the optical three-dimensional structure information if the area where the information values of the optical three-dimensional structure information equal to or greater than the predetermined threshold continue, is smaller than the predetermined range.

3. The optical three-dimensional structure measuring device according to claim 1, further comprising
a computer graphic image building device for applying a rendering process to the optical three-dimensional structure information to build a computer graphic image.

4. The optical three-dimensional structure measuring device according to claim 2, further comprising
a computer graphic image building device for applying a rendering process to the optical three-dimensional structure information to build a computer graphic image.

5. The optical three-dimensional structure measuring device according to claim 3,
wherein the attribute adding device adds attributes that can identify the specific layer area and the regions of interest to the specific layer area and the regions of interest, and
wherein the computer graphic image building device applies a rendering process to the optical three-dimensional structure information to build the computer graphic image including the specific layer area and the regions of interest at least provided with the attributes.

6. The optical three-dimensional structure measuring device according to claim 4,
wherein the attribute adding device adds attributes that can identify the specific layer area and the regions of interest to the specific layer area and the regions of interest, and
wherein the computer graphic image building device applies a rendering process to the optical three-dimensional structure information to build the computer graphic image including the specific layer area and the regions of interest at least provided with the attributes.

7. The optical three-dimensional structure measuring device according to claim 5, wherein
the computer graphic image building device builds, as the computer graphic image, a projection image projecting the specific layer area in the depth direction of the lamination of the measurement target.

8. The optical three-dimensional structure measuring device according to claim 6, wherein
the computer graphic image building device builds, as the computer graphic image, a projection image projecting the specific layer area in the depth direction of the lamination of the measurement target.

9. The optical three-dimensional structure measuring device according to claim 5, wherein
the computer graphic image building device applies a rendering process to the optical three-dimensional structure information to build an optical three-dimensional structure image as the computer graphic image.

10. The optical three-dimensional structure measuring device according to claim 6, wherein
the computer graphic image building device applies a rendering process to the optical three-dimensional structure information to build an optical three-dimensional structure image as the computer graphic image.

11. The optical three-dimensional structure measuring device according to claim 7, wherein
the computer graphic image building device applies a rendering process to the optical three-dimensional structure information to build an optical three-dimensional structure image as the computer graphic image.

12. The optical three-dimensional structure measuring device according to claim 8, wherein
the computer graphic image building device applies a rendering process to the optical three-dimensional structure information to build an optical three-dimensional structure image as the computer graphic image.

13. The optical three-dimensional structure measuring device according to claim 5, wherein
the attribute adding device comprises an attribute controlling device for setting, as the attribute of the specific layer area, an attribute of the regions of interest smaller than a minimum range determination reference value at least among the predetermined range determination reference values.

14. The optical three-dimensional structure measuring device according to claim 6, wherein
the attribute adding device comprises an attribute controlling device for setting, as the attribute of the specific layer area, an attribute of the regions of interest smaller than a minimum range determination reference value at least among the predetermined range determination reference values.

15. The optical three-dimensional structure measuring device according to claim 14, wherein
the attribute controlling device adds different attributes to each of the regions of interest classified by the region-of-interest classifying device based on a plurality of range determination reference values with values greater than the minimum range determination reference value among the predetermined range determination reference values.

16. The optical three-dimensional structure measuring device according to claim 1, wherein
the region-of-interest classifying device classifies the region of interest that is equal to or greater than the second range determination reference value among the predetermined range determination reference values into a cancer invasion area.

17. The optical three-dimensional structure measuring device according to claim 1, further comprising
a new blood vessel distribution image generating device for generating a distribution of the new blood vessel area determined by the region-of-interest classifying device as a new blood vessel distribution image in the specific layer area.

18. A structure information processing method of an optical three-dimensional structure measuring device that directs measurement light in a depth direction of a lamination of a measurement target with a layer structure and that two-dimensionally scans an optical axis of the measurement light to acquire optical three-dimensional structure information of the measurement target, the structure information processing method comprising:
an optical three-dimensional structure information storing step of storing the optical three-dimensional structure information;
a specific layer extracting step of comparing information values of the optical three-dimensional structure information stored in the optical three-dimensional structure information storing step with a predetermined threshold and extracting, as a specific layer area of the measurement target, an area equal to or greater than a predetermined range where the information values of the optical three-dimensional structure information equal to or greater than the predetermined threshold continue;
a missing area extracting step of extracting, as missing areas, areas where the information values of the optical three-dimensional structure information are smaller than the predetermined threshold in the specific layer area;

a missing area range calculating step of calculating sizes of ranges of the missing areas; and a region-of-interest classifying step of comparing the sizes of the ranges of the missing areas with a plurality of predetermined range determination reference values, and classifying the missing areas into a plurality of types of regions of interest of classes corresponding to the sizes of the ranges of the missing areas, wherein the region-of-interest classifying step compares the sizes of the ranges of the missing areas with a first range determination reference value and a second range determination reference value which are among the predetermined range determination reference values, and the structure information processing method of the optical three-dimensional structure measuring device further comprising:

an attribute adding step for adding the same attribute as the specific layer area to the missing area whose size is less than the first range determination reference value to delete the missing area, and for adding a different attribute from the specific layer area to the missing area whose size is the second range determination reference value or more.

19. The structure information processing method according to claim 18, wherein the specific layer extracting step comprises:

determining an area as a noise area to delete the area from the optical three-dimensional structure information if the area where the information values of the optical three-dimensional structure information equal to or greater than the predetermined threshold continue, is smaller than the predetermined range.

20. The structure information processing method according to claim 18, further comprising:

a computer graphic image building step for applying a rendering process to the optical three-dimensional structure information to build a computer graphic image.

* * * * *